United States Patent [19]
Ni et al.

[11] Patent Number: 5,942,417
[45] Date of Patent: Aug. 24, 1999

[54] CD44-LIKE PROTEIN AND NUCLEIC ACIDS

[75] Inventors: Jian Ni, Rockville; Reiner L. Gentz, Silver Spring; Patrick J. Dillon, Gaithersburg, all of Md.

[73] Assignee: Human Genome Sciences, Inc., Rockville, Md.

[21] Appl. No.: 08/892,880

[22] Filed: Jul. 15, 1997

Related U.S. Application Data

[60] Provisional application No. 60/021,762, Jul. 15, 1996.

[51] Int. Cl.$^6$ .......................... C12N 15/00; C07H 21/04; C07K 1/00
[52] U.S. Cl. ................. 435/69.1; 435/70.1; 435/71.1; 435/252.3; 435/320.1; 435/325; 530/350; 530/387.1; 536/23.5; 536/24.3; 536/24.31
[58] Field of Search .................................. 435/69.1, 70.1, 435/71.1, 325, 252.3, 320.1; 536/23.5, 24.3, 24.31, 24.33; 530/350, 387.1

[56] References Cited

U.S. PATENT DOCUMENTS 5,504,194  4/1996  St. John et al. ........................ 530/395

FOREIGN PATENT DOCUMENTS

| WO 93/17047 | 9/1993 | WIPO . |
| WO 94/09811 | 5/1994 | WIPO . |
| WO 95/19183 | 7/1995 | WIPO . |
| WO 95/24913 | 9/1995 | WIPO . |
| WO 95/31544 | 11/1995 | WIPO . |

OTHER PUBLICATIONS

Genbank Report, Accession No. AA046671, Hillier et al. (Sep. 1996).
Genbank Report, Accession No. AA081351, Hillier et al. (Oct. 1996).
Genbank Report, Accession No. AA046747, Hillier et al. (Sep. 1996).
Genbank Report, Accession No. N69434, Hillier et al. (Mar. 1996).
Genbank Report, Accession No. W69477, Hillier et al. (Jun. 1996).
Genbank Report, Accession No. H69328, Hillier et al. (Oct. 1995).
Genbank Report, Accession No. W03259, Hillier et al. (Apr. 1996).
Genbank Report, Accession No. W03670, Hillier et al. (Apr. 1996).
Genbank Report, Accession No. H59965, Hillier et al. (Oct. 1995).
Genbank Report, Accession No. N80143, Hillier et al. (Apr. 1996).
Genbank Report, Accession No. W87511, Hillier et al. (Feb. 1997).
Genbank Report, Accession No. H93850, Hillier et al. (Dec. 1995).
Genbank Report, Accession No. AA463325, Hillier et al. (Jun. 1997).
Genbank Report, Accession No. AA340162, Adams et al. (Apr. 1997).
Genbank Report, Accession No D79275, Fujiwara et al. (Feb. 1996).
Genbank Report, Accession No. H72432, Hillier et al. (Oct. 1995).
Genbank Report, Accession No. R71437, Hillier et al. (Jun. 1995).
Genbank Report, Accession No. R93568, Hillier et al. (Aug. 1995).
Genbank Report, Accession No. H02824, Hillier et al. (Jun. 1995).
Genbank Report, Accession No. AA297240, Adams et al. (Apr. 1997).
Genbank Report, Accession No. H80143, Hillier et al. (Nov. 1995).
Genbank Report, Accession No. D63040, Fujiwara et al. (Aug. 1995).
Genbank Report, Accession No. H02823, Hillier et al. (Jun. 1995).
Genbank Report, Accession No. T96905, Hillier et al. (Mar. 1995).
Genbank Report, Accession No. H93538, Hillier et al. (Dec. 1995).
Genbank Report, Accession No. T40526, Hillier et al. (Jan. 1995).
Genbank Report, Accession No. AA135754, Hillier et al. (May 1997).
Genbank Report, Accession No. D62918, Fujiwara et al. (Aug. 1995).
Genbank Report, Accession No. R71091, Hillier et al. (Jun. 1995).
Genbank Report, Accession No. W69476, Hillier et al. (Jun. 1996).
Genbank Report, Accession No. AA081350, Hillier et al. (Oct. 1996).
Genbank Report, Accession No. H72343, Hillier et al. (Oct. 1995).
Genbank Report, Accession No. D62168, Fujiwara et al. (Aug. 1995).
Genbank Report, Accession No. T96904, Hillier et al. (Mar. 1995).
Genbank Report, Accession No. T39345, Hillier et al. (Jan. 1995).
Genbank Report, Accession No. R81660, Hillier et al. (Jun. 1995).

(List continued on next page.)

*Primary Examiner*—Kenneth R. Horlick
*Attorney, Agent, or Firm*—Sterne, Kessler, Goldstein & Fox P.L.L.C.

[57] ABSTRACT

The present invention concerns a novel CD44-like protein receptor. In particular, isolated nucleic acid molecules are provided encoding the CD44-like protein. CD44-like polypeptides are also provided, as are screening methods for identifying agonists and antagonists capable of enhancing or inhibiting CD44-like protein-mediated signaling. The invention further concerns therapeutic methods for treating diseases associated with processes mediated by CD44-like protein signaling.

87 Claims, 5 Drawing Sheets

OTHER PUBLICATIONS

Genbank Report, Accession No. R24376, Hillier et al. (Apr. 1995).

Genbank Report, Accession No. R96867, Hillier et al. (Sep. 1995).

Arch, R. et al., "Participation in Normal Immune Responses of a Metastasis–Inducing Splice Variant of CD44," *Science* 257:682–685 (1992).

Aruffo, A. et al., "CD44 Is the Principal Cell Surface Receptor for Hyaluronate," *Cell* 61:1303–1313 (1990).

Biocentury, The Bernstein Report on BioBusiness, Jan. 29, 1996.

Carter, W.G. and Wayner, E.A., "Characterization of the Class III Collagen Receptor, a Phosphorylated, Transmembrane Glycoprotein Expressed in Nucleated Human Cells," *J. Bio. Chem.* 263:4193–4201 (1988).

East,J.A. and Hart, I.R., "CD44 and its Role in Tumour Progression and Metastasis," *Eur. J. Cancer* 29A(14):1921–1922 (1993).

Goldstein, L.A. et al., "A Human Lymphocyte Homing Receptor, the Hermes Antigen, Is Related to Cartilage Proteoglycan Core and Link Proteins," *Cell* 56:1063–1072 (1989).

Günthert, U. et al., "A New Variant of Glycoprotein CD44 Confers Metastatic Potential to Rat Carcinoma Cells," *Cell* 65:13–24 (1991).

Gyuris, J. et al., "Cdi1, a Human G1 and S Phase Protein Phosphatase That Associates with Cdk2," *Cell* 75:791–803 (1993).

Haynes, B.F. et al., "CD44 — A molecule involved in leukocyte adherence and T–cell activation," *Immunology Today* 10:423–428 (1989).

Herrlich, P. et al., "CD44 splice variants: metastases meet lymphocytes," *Immunology Today* 14(8):395–399 (1993).

Jain, M. et al., "Role of CD44 in the Reaction of Vascular Smooth Muscle Cells to Arterial Wall Injury," *J. Clin. Invest.* 97(3):596–603 (Feb. 1996).

Jalkanen, S. et al., "Lymphocyte Recognition of High Endothelium: Antibodies to Distinct Epitopes of an 85–90–kD Glycoprotein Antigen Differentially Inhibit Lymphocyte Binding to Lymph Node, Mucosal, or Synovial Endothelial Cells," *J. Cell Bio.* 105:983–990 (1987).

Jalkanen, S. et al., "Biochemical Properties of Glycoproteins Involved in Lymphocyte Recognition of High Endothelial Venules In Man," *J. Immuno.* 141:1615–1623 (1988).

Lazaar, A.L. et al., "T Lymphocytes Adhere to Airway Smooth Muscle Cells Via Integrins and CD44 and Induce Smooth Muscle Cell DNA Synthesis," *J. Exp. Med.* 180:807–816 (1994).

Lesley, J. et al., "CD44 and Its Interaction with Extracellular Matrix," *Adv. Immuno.* 54:271–335 (1993).

Mackay, C.R. et al., "Expression and Modulation of CD44 Variant Isoforms in Humans," *J. Cell Bio.* 124(1&2):71–82 (1994).

Masellis–Smith, A. et al., "Hyaluronan–Dependent Motility of B Cells and Leukemic Plasma Cells in Blood, But Not of Bone Marrow Plasma Cells, in Multiple Myeloma: Alternative Use of Receptor for Hyaluronan–Mediated Motility (RHAMM) and CD44," *Blood* 87(5):1891–1899 (Mar. 1996).

Miyake, K. et al., "Monoclonal Antibodies to Pgp–1/CD44 Block Lympho–Hemopoiesis in Long–term Bone Marrow Cultures," *J. Exp. Med.* 171:477–488 (1990).

Miyake, K. et al., "Hyaluronate Can Function as a Cell Adhesion Molecule and CD44 Participates in Hyaluronate Recognition," *J. Exp. Med.* 172:69–75 (1990).

Moll, J. et al., "Accelerated Immune Response in Transgenic Mice Expressing Rat CD44v4–v7 on T Cells," *J. Immuno.* 156:2085–2094 (Mar. 1996).

Okada, H. et al., "Anti–(glioma surface antigen) monoclonal antibody G–22 recognizes overexpressed CD44 in glioma cells," *Cancer Immunol. Immunother.* 39:313–317 (1994).

Ruiz, P. et al., "CD44 isoforms during differentiation and development," *BioEssays* 17(1):17–24 (1995).

Screaton, G.R. et al., "The Identification of a New Alternative Exon with Highly Restricted Tissue Expression in Transcripts Encoding the Mouse Pgp–1 (CD44) Homing Receptor," *J. Bio. Chem.* 268(17):12235–12238 (1993).

Telen, M.J. et al., "A Blood Group–related Polymorphism of CD44 Abolishes A Hyaluronan–binding Consensus Sequence without Preventing Hyaluronan Binding," *J. Bio. Chem.* 271(12):7147–7153 (Mar. 1996).

Webb, D.S.A. et al., "LFA–3, CD44, and CD45: Physiologic Triggers of Human Monocyte TNF and IL–1 Release," *Science* 249:1295–1297 (1990).

Weber, G.F. et al., "Receptor–Ligand Interaction Between CD44 and Osteopontin (Eta–1)," *Science* 271:509–512 (Jan. 1996).

Yang, B. et al., "Identification of Two Hyaluronan–binding Domains in the Hyaluronan Receptor RHAMM," *J. Bio. Chem.* 268(12):8617–8623 (1993).

```
                    10                    30                    50
        ACGAGCATCCGGACTAGTTATTGAGCATCTGCCTCTCATATCACCAGTGGCCATCTGAGG
                    70                    90                   110
        TGTTTCCCTGGCTCTGAAGGGGTAGGCACGATGGCCAGGTGCTTCAGCCTGGTGTTGCTT
                                               M  A  R  C  F  S  L  V  L  L
                   130                   150                   170
        CTCACTTCCATCTGGACCACGAGGCTCCTGGTCCAAGGCTCTTTGCGTGCAGAAGAGCTT
        L  T  S  I  W  T  T  R  L  L  V  Q  G  S  L  R  A  E  E  L
                   190                   210                   230
        TCCATCCAGGTGTCATGCAGAATTATGGGGATCACCCTTGTGAGCAAAAAGGCGAACCAG
        S  I  Q  V  S  C  R  I  M  G  I  T  L  V  S  K  K  A  N  Q
                   250                   270                   290
        CAGCTGAATTTCACAGAAGCTAAGGAGGCCTGTAGGCTGCTGGGACTAAGTTTGGCCGGC
        Q  L  N  F  T  E  A  K  E  A  C  R  L  L  G  L  S  L  A  G
                   310                   330                   350
        AAGGACCAAGTTGAAACAGCCTTGAAAGCTAGCTTTGCAACTTGCAGCTATGGCTGGGTT
        K  D  Q  V  E  T  A  L  K  A  S  F  A  T  C  S  Y  G  W  V
                   370                   390                   410
        GGCGATGGATTCGTGGTCATCTCTAGGATTAGCCCAAACCCCAAGTGTGGGAAAAATGGG
        G  D  G  F  V  V  I  S  R  I  S  P  N  P  K  C  G  K  N  G
                   430                   450                   470
        GTGGGTGTCCTGATTTGGAAGGTTCCAGTGAGCCGACAGTTTGCAGCCTATTGTTACAAC
        V  G  V  L  I  W  K  V  P  V  S  R  Q  F  A  A  Y  C  Y  N
                   490                   510                   530
        TCATCTGATACTTGGACTAACTCGTGCATTCCAGAAATTATCACCACCAAAGATCCCATA
        S  S  D  T  W  T  N  S  C  I  P  E  I  I  T  T  K  D  P  I
                   550                   570                   590
        TTCAACACTCAAACTGCAACACAAACAACAGAATTTATTGTCAGTGACAGTACCTACTCG
        F  N  T  Q  T  A  T  Q  T  T  E  F  I  V  S  D  S  T  Y  S
                   610                   630                   650
        GTGGCATCCCCTTACTCTACAATACCTGCCCCTACTACTACTCCTCCTGCTCCAGCTTCC
        V  A  S  P  Y  S  T  I  P  A  P  T  T  T  P  P  A  P  A  S
                   670                   690                   710
        ACTTCTATTCCACGGAGAAAAAAATTGATTTGTGTCACAGAAGTTTTTATGGAAACTAGC
        T  S  I  P  R  R  K  K  L  I  C  V  T  E  V  F  M  E  T  S
                   730                   750                   770
        ACCATGTCTACAGAAACTGAACCATTTGTTGAAAATAAAGCAGCATTCAAGAATGAAGCT
        T  M  S  T  E  T  P  F  V  E  N  K  A  A  F  K  N  E  A
                   790                   810                   830
        GCTGGGTTTGGAGGTGTCCCCACGGCTCTGCTAGTGCTTGCTCTCCTCTTCTTTGGTGCT
        A  G  F  G  G  V  P  T  A  L  L  V  L  A  L  L  F  F  G  A
                   850                   870                   890
        GCAGCTGGTCTTGGATTTTGCTATGTCAAAAGGTATGTGAAGGCCTTCCCTTTTACAAAC
        A  A  G  L  G  F  C  Y  V  K  R  Y  V  K  A  F  P  F  T  N
                   910                   930                   950
        AAGAATCAGCAGAAGGAAATGATCGAAACCAAAGTAGTAAAGGAGGAGAAGGCCAATGAT
        K  N  Q  Q  K  E  M  I  E  T  K  V  V  K  E  E  K  A  N  D
                   970                   990                  1010
        AGCAACCCTAATGAGGAATCAAAGAAAACTGATAAAAACCCAGAAGAGTCCAAGAGTCCA
        S  N  P  N  E  E  S  K  K  T  D  K  N  P  E  E  S  K  S  P
```

FIG.1A

```
          1030                1050                1070
AGCAAAACTACCGTGCGATGCCTGGAAGCTGAAGTTTAGATGAGACAGAAATGAGGAGAC
 S  K  T  T  V  R  C  L  E  A  E  V  *
          1090                1110                1130
ACACCTGAGGCTGGTTTCTTTCATGCTCCTTACCCTGCCCCAGCTGGGGAAATCAAAAGG
          1150                1170                1190
GCCAAAGAACCAAAGAAGAAAGTCCACCCTTGGTTCCTAACTGGAATCAGCTCAGGACTG
          1210                1230                1250
CCATTGGACTATGGAGTGCACCAAAGAGAATGCCCTTCTCCTTATTGTAACCCTGTCTGG
          1270                1290                1310
ATCCTATCCTCCTACCTCCAAAGCTTCCCACGGCCTTTCTAGCCTGGCTATGTCCTAATA
          1330                1350                1370
ATATCCCACTGGGAGAAAGGAGTTTTGCAAAGTGCAAGGACCTAAAACATCTCATCAGTA
          1390                1410                1430
TCCAGTGGTAAAAAGGCCTCCTGGCTGTCTGAGGCTAGGTGGGTTGAAAGCCAAGGAGTC
          1450                1470                1490
ACTGAGACCAAGGCTTTCTCTACTGATTCCGCAGCTCAGACCCTTTCTTCAGCTCTGAAA
          1510                1530                1550
GAGAAACACGTATCCCACCTGACATGTCCTTCTGAGCCCGGTAAGAGCAAAAGAATGGCA
          1570                1590                1610
GAAAAGTTTAGCCCCTGAAAGCCATGGAGATTCTCATAACTTGAGACCTAATCTCTGTAA
          1630                1650                1670
AGCTAAAATAAAGAAATAGAACAAGGCTGAGGATACGACAGTACACTGTCAGCAGGGACT
          1690                1710                1730
GTAAACACAGACAGGGTCCAAGTGTTTTCTCTGAACACATTGAGTTGGAATCACTGTTTA
          1750                1770                1790
GAACACACACACTTACTTTTTCTGGTCTCTACCACTGCTGATATTTTCTCTAGGAAATAT
          1810                1830                1850
ACTTTTACAAGTAACAAAAATAAAAACTCTTATAAATTTCTATTTTTATCTGAGTTACAG
          1870                1890                1910
AAATGATTACTAAGGAAGATTACTCAGTAATTTGTTTAAAAAGTAATAAAATTCAACAAA
          1930                1950                1970
CATTTGCTGAATAGCTACTATATGTCAAGTGCTGTGCAAGGTATTACACTCTGTAATTGA
          1990                2010                2030
ATATTATTCCTCAAAAAATTGCACATAGTAGAACGCTATCTGGGAAGCTATTTTTTTCAG
          2050                2070                2090
TTTTGATATTTCTAGCTTATCTACTTCCAAACTAATTTTTATTTTTGCTGAGACTAATCT
          2110                2130                2150
TATTCATTTTCTCTAATATGGCAACCATTATAACCTTAATTTATTATTAACATACCTAAG
          2170                2190                2210
AAGTACATTGTTACCTCTATATACCAAAGCACATTTTAAAAGTGCCATTAACAAATGTAT
          2230                2250                2270
CACTAGCCCTCCTTTTTCCAACAAGAAGGGACTGAGAGATGCAGAAATATTTGTGACAAA
          2290
AAATTAAAGCATTTAGAAAAAAAAAAAAAAAAA
```

FIG. 1B

```
  1 MARCFSLVLLLTSIWTTRLLVQGSLRAEELSIQVSCRIMGITLVSKKANQ 50
     :. |:: |. |.   |:| ||  .::::.:.||. |:   |.|.:.
  1 ....MDKVWWHTA.WGLLCLLQLSLAQQQIDLNITCRYAGVFHVEKNGRY 45

51 QLNFTEAKEACRLLGLSLAGKDQVETALKASFATCSYGWVGDGFVVISRI 100
     :. ||| : |  :. .|:...|:| ||: :|.||.||:: :| |||.||
 46 SISRTEAADLCEAFNTTLPTMAQMELALRKGFETCRYGFI.EGHVVIPRI 94

101 SPNPKCGKNGVGVLIWKVPVSRQFAAYCYNSSDTWTNSCIP......... 141
     ||: |: |..||.|:  .  .::..||:|.|...:.|..
 95 HPNAICAANNTGVYILLASNTSHYDTYCFNASAPLEEDCTSVTDLPNSFD 144

142 .....EIITTKDPIFNTQTA..TQTTEFIVSDSTYSVASPYSTIPAPT.. 182
          .|:. .::  :.....  |: .:: .|: . ..|. |||. .|
145 GPVTITIVNRDGTRYSKKGEYRTHQEDIDASNIIDEDVSSGSTIEKSTPE 194

183 .....TTPPAPASTSIPRRKKLICVTEVFMETSTMSTETEPFVENKAAFK 227
          |. |....|: .| ::.....:   : |.. :::. ...:| :
195 GYILHTDLPTSQPTG.DRDDAFFIGSTLATGHSSGNQDSGVTTTSGPARR 243

228 NEAAGFGGVPTALLVLALLFFGAAAGLGFCYVKRYVKAFPFTNKNQQKEM 277
     : :::   : ..||.|||::   |...:.   :|..  .:  | ...:
244 PQIPEWLIILASLLALALIL...AVCIAVNSRRRCGQKKKLV.INSGNGT 289

278 IETKVVKEEKANDSNPNEESKKTDKNPEESKSPSKTT.....VRCLEAEV 322
     :|.: ..| .:::.|...|  . .:|:|.|.... .|.    :.::: ::
290 VEDRKPSELNGEASKSQEMVHLVNKEPTETPDQFMTADETRNLQSVDMKI 339
```

FIG.2

CD44-LIKE PROTEIN AND NUCLEIC ACIDS

This application claims the benefit of the filing date of provisional application 60/021,762 filed on Jul. 15, 1996, which is herein incorporated by reference.

BACKGROUND OF THE INVENTION

1. Field of the Invention

The present invention relates to a novel CD44-like protein receptor. In particular, isolated nucleic acid molecules are provided encoding the CD44-like protein. CD44-like protein polypeptides are also provided, as are screening methods for identifying agonists and antagonists capable of enhancing or inhibiting CD44-like protein-mediated signaling. The invention further concerns therapeutic methods for treating diseases associated with processes mediated by CD44-like protein signaling.

2. Background Information

CD44 (also known as Pgp-1, Hermes-3, HCAM, ECMR III) is a widely expressed glycoprotein with a molecular weight of 85 to 90 kDa (Haynes et al., *Immunol. Today* 10:423–428 (1989)). Immunological studies have shown that CD44 is involved in a diverse range of biological functions such as lymphocyte binding to high endothelial venules (Jalkanen et al., *J. Cell. Biol.* 105:983–990 (1987)), lymphopoiesis (Miyake et al., J. Exp. Med 171:477–488 (1990)) and activation of leukocytes (Webb et al., *Science* 249:1295–1297 (1990)). CD44 has also been shown to play a role in extracellular matrix binding, cell migration, lymphocyte activation, lymphocyte homing, and proliferation of bronchial smooth muscle cell (Herrlich et al., *Immunology Today,* 14(8):395–399, (1993); Lesley et al., *Immunology,* 54:271–355, (1993); Lazzar et al., *Journal of Experimental Medicine,* 180:807–816 (1994)). A splice variant of CD44, CD44-V6, has been shown to play a role in tumor cell metastasis (Gunthert et al., *Cell,* 65:13–24 (1991)). The CD44 cDNA sequence has revealed a domain of some 90 amino acids near the N-terminus bearing a significant similarity to the link and core proteins in proteoglycan (Goldstein et al., *Cell* 56:1063–1072 (1989)), leading to the determination that hyaluronate, a major component of the extacellular matrix, is a ligand for CD44 (Miyake et al., *J. Exp. Med* 172:69–75 (1990); Aruffo et al., *Cell* 61:1303–1313 (1990)). Fibronectin and collagen type I and VI have also been shown to interact with CD44 (Carter et al., *J. Biol. Chem.* 263:4193–4201 (1988)).

CD44 is a widely distributed heterogenous population of cell surface adhesion molecules. The CD44 gene has twenty exons, ten of which encode the sequence for standard CD44. An additional ten variable exons are inserted by alternative splicing.

Although the standard 85 kDa CD44 is broadly expressed by many different types of cells, the expression of CD44 variants is rather limited. Arch et al. have demonstrated a transient expression of a CD44 variant, V6, in leukocytes from animals after allogeneic immunization (Arch et al., *Science* 257:682–685 (1992)), indicating a possible role for this variant in mediating leukocyte trafficking.

Initially, the heterogeneity of CD44 was thought to be due to post-translation modification, especially the addition of chondroitin sulfate, which gives rise to a higher molecular weight from of about 200 kDa (Jalkanen et al., *J. Immunol.* 141:1615–1623 (1998)). The finding of a protein isoform in rats capable of conferring metastatic potential to nonmetastatic cells established a new role for CD44, namely, regulating cell migration (Gunthert et al., *Cell* 65:13–24 (1991)).

Interestingly, several recent studies have ascribed unique functional activities to certain alternatively spliced isoforms, raising the possibility that the inclusion of additional peptide sequences within the extracellular domain of CD44 may alter the ligand-binding specificity of the molecule. As an example, CD44H, the major CD44 isoform present on resting hemopoietic cells, and CD44R1, a differentially expressed isoform containing a 132 amino acid insertion coded by the alternatively spliced exons v8-v10, can bind both immobilized and soluble hyaluronan when transfected into the CD44-negative murine lymphoma cell line TIL1. However, only the expression of CD44R1 can induce these cells to homotypically aggregate. This homotypic aggregation may be mediated by the adhesive interaction between a determinant encoded by the insertion region present in CD44R1 and a common region present in both CD44R1 and CD44H.

Different isoforms of CD44 are often preferentially expressed by certain cell types. A widely expressed CD44 isoform is the "standard" or "hematopoietic" CD44 (CD44s) molecule, which is encoded by exons 1–5, 15–17 and 19 of the CD44 gene. This 85–95 kDa molecule is the principle CD44 isoform on hematopoietic cells and lymphocytes. Larger CD44 variants that contain different combinations of alternatively spliced exons are preferentially expressed on epithelial cells, but they can also be found on activated lymphocytes and high grade malignant lymphomas.

From the above, it will be understood by one of ordinary skill in the art that the identification of additional CD44 variants and CD44 homologues is of great importance.

SUMMARY OF THE INVENTION

The present invention provides isolated nucleic acid molecules comprising a nucleic acid sequence encoding a CD44-like protein whose amino acid sequence is shown in FIGS. 1A–1B [SEQ ID NO:2] or a fragment of the polypeptide. The CD44-like protein gene contains an open reading frame encoding a protein of about 322 amino acid residues whose initiation codon is at position 91–93 of the nucleotide sequence shown in FIGS. 1A–1B [SEQ ID NO:1], with a leader sequence of about 21 amino acid residues, and a deduced molecular weight of about 35 kDa. The amino acid sequence of the mature CD44-like protein is shown in FIGS. 1A–1B as amino acid residues from about 22 to about 322 [amino acid residues from about 1 to about 301 in SEQ ID NO:2].

In another aspect, the invention provides isolated nucleic acid molecules encoding the CD44-like polypeptide having an amino acid sequence encoded by the cDNA of the clone deposited as ATCC Deposit No. 97520 on Apr. 25, 1996.

Preferably, the nucleic acid molecule will encode the mature polypeptide encoded by the above-described deposited cDNA.

Thus, one aspect of the invention provides an isolated nucleic acid molecule comprising a polynucleotide having a nucleotide sequence selected from the group consisting of: (a) a nucleotide sequence encoding the CD44-like protein having the complete amino acid sequence in SEQ ID NO:2; (b) a nucleotide sequence encoding the CD44-like protein having the complete amino acid sequence in SEQ ID NO:2 but minus the N-terminal methionine residue; (c) a nucleotide sequence encoding the mature CD44-like protein having the amino acid sequence at positions from about 1 to about 301 in SEQ ID NO:2; (d) a nucleotide sequence encoding the CD44-ike protein having the complete amino acid sequence encoded by the cDNA clone contained in ATCC Deposit No. 97520; (e) a nucleotide sequence encoding the mature CD44-like protein having the amino acid sequence encoded by the cDNA clone contained in ATCC Deposit No. 97520; (f) a nucleotide sequence encoding the CD44-like protein extracellular domain; (g) a nucleotide sequence encoding the CD44-like protein transmembrane domain; (h) a nucleotide sequence encoding the CD44-like protein intracellular domain; (i) a nucleotide sequence encoding the CD44-like protein intracellular and extracellular domains with all or part of the transmembrane domain deleted; and (j) a nucleotide sequence complementary to any of the nucleotide sequences in (a), (b), (c), (d), (e), (f), (g), (h), or (i), above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), (f), (g), (h), (i), or (j), above, or a polynucleotide which hybridizes under stringent hybridization conditions to a polynucleotide in (a), (b), (c), (d), (e), (f), (g), (h), (i), or (j), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CD44-like protein having an amino acid sequence in (a), (b), (c), (d), (e), (f), (g), (h), or (i) above.

The present invention also relates to vectors which include the isolated DNA molecules of the present invention, host cells which are genetically engineered with the recombinant vectors, and the production of CD44-like polypeptides or fragments thereof by recombinant techniques.

The invention further provides an isolated CD44-like protein having an amino acid sequence selected from the group consisting of: (a) the amino acid sequence of the CD44-like protein having the complete 322 amino acid sequence, including the leader sequence shown in SEQ ID NO:2; (b) the amino acid sequence of the CD44-like protein having the complete 322 amino acid sequence, including the leader sequence shown in SEQ ID NO:2 but minus the N-terminal methionine residue; (c) the amino acid sequence of the mature CD44-like protein (without the leader) having the amino acid sequence at positions from about 1 to about 301 in SEQ ID NO:2; (d) the amino acid sequence of the CD44-like protein having the complete amino acid sequence (including the leader) encoded by the cDNA clone contained in ATCC Deposit No. 97520; (e) the amino acid sequence of the mature CD44-like protein having the amino acid sequence encoded by the cDNA clone contained in ATCC Deposit No. 97520; (f) the amino acid sequence of the CD44-like protein extracellular domain; (g) the amino acid sequence of the CD44-like protein transmembrane domain; (h) the amino acid sequence of the CD44-like protein intracellular domain; and (i) the amino acid sequence of the CD44-like protein intracellular and extracellular domains with all or part of the transmembrane domain deleted.

The polypeptides of the present invention also include polypeptides having an amino acid sequence which are at least 95% identical, and still more preferably 96%, 97%, 98% or 99% identical to those above.

An additional embodiment of this aspect of the invention relates to a peptide or polypeptide which has the amino acid sequence of an epitope-bearing portion of a CD44-like protein having an amino acid sequence described in (a), (b), (c), (d), (e), (f), (g), (h), or (i) above. Peptides or polypeptides having the amino acid sequence of an epitope-bearing portion of a CD44-like protein of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a CD44-like protein having an amino acid sequence described in (a), (b), (c), (d), (e), (f), (g), (h), or (i) above. Such antibodies are useful diagnostically or therapeutically as described below.

The invention also provides methods for administering an antagonist of the CD44-like protein receptor to inhibit the CD44-like protein signaling pathway. Such methods are useful for suppressing or inhibiting cell migration, inflammation, cell adhesion and T-cell activation. Preferably, by the invention, the method for inhibiting cell migration relates to treating cancer, metastasis, arteriosclerosis, or vascular restenosis and the method for inhibiting inflammation relates to treating graft versus host disease and rheumatoid arthritis.

The invention further provides a method for increasing cell migration by administering a therapeutically effective amount of an agonist of the CD44-like protein mediated signaling pathway. Preferably, the method of increasing cell migration is used to improve wound healing.

The invention further provides a screening method for identifying compounds capable of enhancing or inhibiting a cellular response induced by the CD44-like protein receptor-mediated signaling pathway, which involves contacting cells which express the CD44-like protein receptor with the candidate compound, assaying a cellular response, and comparing the cellular response to a standard cellular response, the standard being assayed when contact is made in absence of the candidate compound; whereby, an increased cellular response over the standard indicates that the candidate compound is an agonist and a decreased cellular response over the standard indicates that the candidate compound is an antagonist.

In another aspect, a screening assay for agonists and antagonists is provided which involves determining the effect a candidate compound has on ligand binding to the CD44-like protein receptor. In particular, the method involves contacting the CD44-like protein receptor with a ligand and a candidate compound and determining whether ligand binding to the CD44-like protein receptor is increased or decreased due to the presence of the candidate compound.

BRIEF DESCRIPTION OF THE FIGURES

FIGS. 1A–1B shows the nucleotide [SEQ ID NO:1] and deduced amino acid [SEQ ID NO:2] sequences of CD44-like protein. The protein has a predicted leader sequence of about 21 amino acid residues (underlined) and a deduced molecular weight of about 35 kDa. It is further predicted that amino acid residues from about 22 to about 238 constitute the extracellular domain (sequence between the first and second underlined sequences) [amino acid residues from about 1 to about 217 in SEQ ID NO:2]; from about 239 to about 266 the transmembrane domain (second underlined sequence) [amino acid residues from about 218 to about 245 in SEQ ID NO:2]; and from about 267 to about 322 the intracellular domain (the remaining sequence) [amino acid residues from about 246 to about 301 in SEQ ID NO:2].

FIG. 2 shows the regions of similarity between the amino acid sequences of CD44-like protein and rat CD44 (deposited in GenBank with the accession number A38745) [SEQ ID NO:3].

FIG. 3A: lane 1, spleen; lane 2, lymph node; lane 3, thymus; lane 4, appendix; lane 5, peripheral blood leukocyte; lane 6, bone marrow; lane 7, fetal liver. FIG. 3B: lane 1, heart; lane 2, brain; lane 3, placenta; lane 4, lung; lane 5, liver; lane 6, skeletal muscle; lane 7, kidney; lane 8, pancreas.

DETAILED DESCRIPTION

Figure 3A:
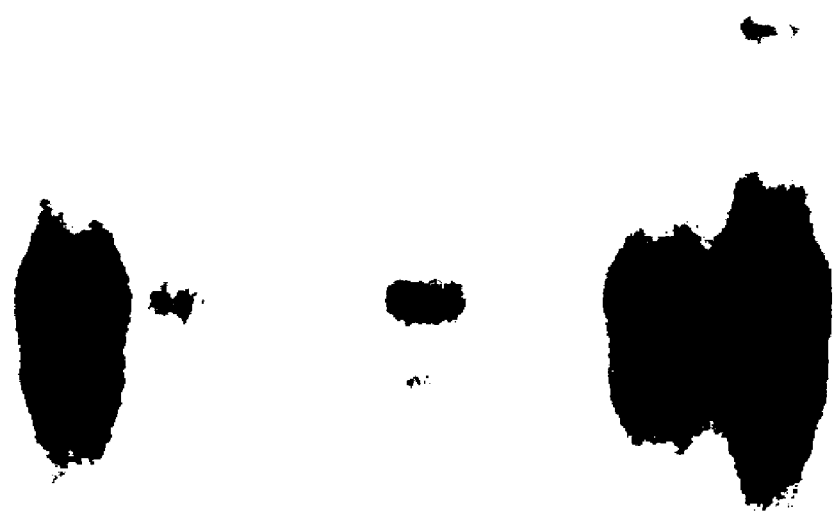
FIGS. 3A and 3B are Northern blots showing the tissue distribution of human CD44-like mRNA expression.

The present invention provides isolated nucleic acid molecules comprising a polynucleotide encoding a CD44-like protein having an amino acid sequence shown in FIGS. 1A–1B [SEQ ID NO:2], which was determined by sequencing a cloned cDNA. The CD44-like protein of the present invention shares sequence homology with the rat cell adhesion molecule CD44 precursor (FIG. 2) [SEQ ID NO:3]. The nucleotide sequence shown in FIGS. 1A–1B [SEQ ID NO:1] was obtained by sequencing the HUVDE75 clone, which was deposited on Apr. 25, 1996, at the American Type Culture Collection, 12301 Park Lawn Drive, Rockville, Md. 20852, and given accession number 97520.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain a some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

Thus, in one aspect, isolated nucleic acid molecules are provided which encode the CD44-like protein. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolate nucleic acid molecules according to the present invention further include such molecules produced synthetically.

Using the information provided herein, such as the nucleotide sequence set out in FIGS. 1A–1B, a nucleic acid molecule of the present invention encoding a CD44-like protein may be obtained using standard cloning and screening procedures, such as those for cloning cDNAs using mRNA as starting material. Illustrative of the invention, the nucleic acid molecule described in FIGS. 1A–1B was discovered in a cDNA library derived from human umbilical vein endothelial cells. Further, the gene was also found in cDNA libraries derived from the following types of human cells: ovarian cancer, breast cancer, prostate, 12 week old early stage fetus, fetal heart, bone cancer, 8 week whole embryo, fetal liver, dura mater, umbilical vein endothelium, placenta, lung, and fetal liver-spleen.

The CD44-like protein gene contains an open reading frame encoding a protein of about 322 amino acid residues whose initiation codon is at position 91–93 of the nucleotide sequence shown in FIGS. 1A–1B [SEQ ID NO:1], with a predicted leader sequence of about 21 amino acid residues, and a deduced molecular weight of about 35 kDa. The amino acid sequence of the predicted mature CD44-like protein is shown in FIGS. 1A–1B, amino acid residues from about 22 to about 322 [amino acid residues from about 1 to about 301 in SEQ ID NO:2]. The mature CD44-like protein has three main structural domains. These include the extracellular domain, which includes the ligand binding domain, and is predicted to correspond to amino acid residues from about 22 to about 238 in FIGS. 1A–1B [amino acid residues from about 1 to about 217 in SEQ ID NO:2]. The mature extracellular domain is predicted to be about 217 amino acids in length with a molecular weight of about 23.5 kDa. Another domain is the transmembrane domain, which has been predicted to correspond to amino acid residues from about 239 to about 266 in FIGS. 1A–1B [amino acid residues from about 218 to about 245 in SEQ ID NO:2]. Another domain is the intracellular domain, which has been predicted to correspond to amino acid residues from about 267 to about 322 in FIGS. 1A–1B [amino acid residues from about 246 to about 301 in SEQ ID NO:2]. It will be appreciated that reasonable persons of skill in the art may disagree, depending on the criteria used, concerning the exact 'address' of the above described CD44-like protein domains. Thus, for example, the exact location of the CD44-like protein extracellular, intracellular and transmembrane domains in FIGS. 1A–1B [SEQ ID NO:2] may vary slightly (e.g., the exact 'address' may differ by about 1 to about 5 residues compared to that shown in FIGS. 1A–1B) depending on the criteria used to define the domain.

The CD44-like protein shown in FIGS. 1A–1B [SEQ ID NO:2] is about 24% identical and about 46% similar to the rat cell adhesion molecule CD44 precursor, which can be accessed on GenBank as Accession No. A38745.

As indicated, the present invention also provides the mature form(s) of the CD44-like protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CD44-like protein polypeptides having the amino acid sequence encoded by the cDNA clone contained in the host identified as ATCC Deposit No. 97520 and as shown in SEQ ID NO:2. By the mature CD44-like protein having the amino acid sequence encoded by the cDNA clone contained in the host identified as ATCC Deposit 97520 is meant the mature form(s) of the CD44-like protein produced by expression in a mammalian cell (e.g., COS cells, as described below) of the complete open reading frame encoded by the human DNA sequence of the clone contained in the vector in the deposited host. As indicated below, the mature CD44-like protein having the amino acid sequence encoded by the cDNA clone contained in ATCC Deposit No. 97520 may or may not differ from the predicted "mature" CD44-like protein shown in SEQ ID NO:2 (amino acids from about 1 to about 301) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch, *Virus Res.* 3:271–286 (1985)) uses the information from a short N-terminal charged region and a subsequent uncharged region of the complete (uncleaved) protein. The method of von Heinje, *Nucleic Acids Res.* 14:4683–4690 (1986)) uses the information from the residues surrounding the cleavage site, typically residues –13 to +2 where +1 indicates the amino acid terminus of the mature protein. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete CD44-like protein of the present invention were analyzed by a computer program (PSORT). This program is available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids –1 and +1 in SEQ ID NO:2. Thereafter, the complete amino acid sequences were further analyzed by visual inspection, applying a simple form of the (–1,–3) rule of von Heine. von Heinje, supra. Thus, the leader sequence for the CD44-like protein is predicted to consist of amino acid residues –21 to –1 in SEQ ID NO:2, while the predicted mature CD44-like protein consists of residues 1 to 301 in SEQ ID NO:2.

As one of ordinary skill would appreciate, due to the possibilities of sequencing errors, as well as the variability of cleavage sites for leaders in different known proteins, the predicted CD44-like protein encoded by the deposited cDNA comprises about 322 amino acids, but may be anywhere in the range of 318–328 amino acids; and the predicted leader sequence of this protein is about 21 amino acids, but may be anywhere in the range of about 17 to about 25 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

Isolated nucleic acid molecules of the present invention include DNA molecules comprising an open reading frame (ORF) whose initiation codon is at position 91–93 of the nucleotide sequence shown in FIGS. 1A–1B [SEQ ID NO:1] and further include DNA molecules which comprise a sequence substantially different than all or part of the ORF whose initiation codon is at position 91–93 of the nucleotide sequence shown in FIGS. 1A–1B [SEQ ID NO:1] but which, due to the degeneracy of the genetic code, still encode the CD44-like protein or a fragment thereof. Of course, the genetic code is well known in the art. Thus, it would be routine for one skilled in the art to generate the degenerate variants described above.

In addition, the invention provides nucleic acid molecules having nucleotide sequences related to extensive portions of SEQ ID NO:1 which have been determined from the following related cDNA clones: HFFAC14R (SEQ ID NO:11), HUVDE75R (SEQ ID NO:12), HPRTI58R (SEQ ID NO:13), HHFCE82F (SEQ ID NO:14), and HE2CJ22R (SEQ ID NO:15).

In another aspect, the invention provides isolated nucleic acid molecules encoding the CD44-like polypeptide having an amino acid sequence encoded by the cDNA of the clone deposited as ATCC Deposit No. 97520 on April 25, 1996. In a further embodiment, nucleic acid molecules are provided encoding the mature CD44-like polypeptide or the full-length CD44-like polypeptide lacking the N-terminal methionine.

The invention further provides an isolated nucleic acid molecule having the nucleotide sequence shown in FIGS. 1A–1B [SEQ ID NO:1] or the nucleotide sequence of the CD44-like protein gene contained in the above-described deposited cDNA, or a nucleic acid having a sequence complementary to one of the above sequences. Such isolated nucleic acid molecules, particularly DNA molecules, are usefl as probes for gene mapping by in situ hybridization with chromosomes and for detecting expression of the CD44-like protein gene in human tissue by Northern blot analysis. As described in detail below, detecting enhanced CD44-like protein gene expression in certain tissues is indicative of certain disorders.

The present invention is further directed to fragments of the isolated nucleic acid molecules described herein. By a fragment of an isolated DNA molecule having the nucleotide sequence of the deposited cDNA or the nucleotide sequence as shown in FIGS. 1A–1B [SEQ ID NO:1] is intended DNA fragments at least 15 nt, and more preferably at least 20 nt, still more preferably at least 30 nt in length which are useful as diagnostic probes and primers as discussed above and in more detail below. Of course larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, or 2296 nt in length are also useful as probes according to the present invention as are DNA fragments corresponding to most, if not all, of the nucleotide sequence of the deposited cDNA or the nucleotide sequence as shown in FIGS. 1A–1B [SEQ ID NO:1]. By a fragment at least 20 nt in length, for example, is intended fragments which include 20 or more contiguous bases from the nucleotide sequence of the deposited cDNA or the nucleotide sequence as shown in FIGS. 1A–1B [SEQ ID NO:1]. Since the gene has been deposited and the nucleotide sequence shown in FIGS. 1A–1B [SEQ ID NO:1] is provided, generating such DNA fragments would be routine to the skilled artisan. For example, restriction endonuclease cleavage or shearing by sonication could easily be used to generate fragments of various sizes. Alternatively, the DNA fragments of the present invention could be generated synthetically according to known techniques.

Preferred nucleic acid fragments of the present invention include nucleic acid molecules encoding: a polypeptide comprising the CD44-like protein extracellular domain [amino acid residues from about 1 to about 217 in SEQ ID NO:2]; a polypeptide comprising the CD44-like protein transmembrane domain [amino acid residues from about 218 to about 245 in SEQ ID NO:2]; a polypeptide comprising the CD44-like protein intracellular domain [amino acid residues from about 246 to about 301 in SEQ ID NO:2; and a polypeptide comprising the CD44-like protein extracellular and intracellular domain having all or part of the transmembrane region deleted.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97520. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1× SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–750 nt in length, or even to the entire length of the reference polynucleotide, also are useful as probes according to the present invention, as are polynucleotides corresponding to most, if not all, of the nucleotide sequence of the deposited cDNA or the nucleotide sequence as shown in FIGS. 1A–1B [SEQ ID NO:1].

By a portion of a polynucleotide of "at least 20 nt in length," for example, is intended 20 or more contiguous nucleotides from the nucleotide sequence of the reference polynucleotide, (e.g., the deposited cDNA or the nucleotide sequence as shown in FIGS. 1A–1B [SEQ ID NO:1]). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Of course, a polynucleotide which hybridizes only to a poly A sequence (such as the 3' terminal poly(A) tract of the CD44-like cDNA shown in FIGS. 1A–1B [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule contain a poly (A) stretch or the complement thereof (e.g., practically any double-stranded cDNA clone).

As indicated, nucleic acid molecules of the present invention which encode the CD44-like protein may include, but are not limited to the coding sequence for the mature polypeptide, by itself; the coding sequence for the mature polypeptide and additional sequences, such as those encoding the about 21 amino acid leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci., USA* 86:821–824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance. Other such fusion proteins include the CD44-like protein fused to Fc at the N- or C-terminus. For example, the extracellular CD44-like protein domain described above has been fused, together with the leader sequence, to Fc at its C-terminus. This construct was successfully expressed recombinantly in CHO cells.

Thus, the polypeptide may be expressed in a modified form, such as a fusion protein, and may include not only secretion signals but also additional heterologous functional regions. In a further example, a region of additional amino acids, particularly charged amino acids, may be added to the N-terminus of the polypeptide to improve stability and persistence in the host cell, during purification or during subsequent handling and storage. Also, as indicated, a region (s) also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in the fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL5. See, D. Bennett et al., *Journal of Molecular Recognition,* Vol. 8 52–58 (1995) and K. Johanson et al., *The Journal of Biological Chemistry,* Vol. 270, No. 16, pp 9459–9471 (1995).

The present invention further relates to variants of the nucleic acid molecules of the present invention, which encode for fragments, analogs or derivatives of the CD44-like protein. Variants may occur naturally, such as an allelic variant. By an "allelic variant" is intended one of several alternate forms of a gene occupying a given locus on a chromosome of an organism. Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Especially preferred among these are silent substitutions, additions and deletions, which do not alter the properties and activities of the CD44-like protein or fragment thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 301 in SEQ ID NO:2; (d) a nucleotide sequence encoding the polypeptide having the amino acid sequence encoded by the cDNA clone contained in ATCC Deposit No. 97520; (e) a nucleotide sequence encoding the mature CD44-like polypeptide having the amino acid sequence encoded by the cDNA clone contained in ATCC Deposit No. 97520; (f) a nucleotide sequence encoding the CD44-like polypeptide extracellular domain; (g) a nucleotide sequence encoding the CD44-like polypeptide transmembrane domain; (h) a nucleotide sequence encoding the CD44-like polypeptide intracellular domain; (i) a nucleotide sequence encoding the CD44-like polypeptide extracellular and intracellular domains with all or part of the transmembrane domain deleted; and (j) a nucleotide sequence complementary to any of the nucleotide sequences in (a), (b), (c), (d), (e), (f), (g), (h), or (i).

By a polynucleotide having a nucleotide sequence at least, for example, 95% "identical" to a reference nucleotide sequence encoding a CD44-like polypeptide is intended that the nucleotide sequence of the polynucleotide is identical to the reference sequence except that the polynucleotide sequence may include up to five point mutations per each 100 nucleotides of the reference nucleotide sequence encoding the CD44-like polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule has a nucleotide sequence at least 95%, 96%, 97%, 98% or 99% identical to, for instance, the nucleotide sequence shown in FIGS. 1A–1B or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (Advances in Applied Mathematics 2: 482–489, 1981) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to such nucleic acid molecules which are at least 95%, 96%, 97%, 98% or 99% identical to a nucleic acid sequence described above irrespective of whether they encode a polypeptide having CD44-like protein activity. This is because, even where a particular nucleic acid molecule does not encode a polypeptide having CD44-like protein activity, one of skill would still know how to use the nucleic acid molecule, for instance, as a hybridization probe or a polymerase chain reaction (PCR) primer. Uses of the nucleic acid molecules of the present invention that do not encode a polypeptide having CD44-like protein activity include, inter alia, (1) isolating the gene encoding the CD44-like protein, or allelic variants thereof from a cDNA library; (2) in situ hybridization (FISH) to metaphase chromosomal spreads to provide precise chromosomal location of the CD44-like gene as described in Verma et al., *Human Chromosomes: a Manual of Basic Techniques,* Pergamon Press, New York (1988); and (3) Northern blot analysis for detecting expression of CD44-like mRNA in specific tissues.

Preferred, however, are nucleic acid molecules which are at least 95%, 96%, 97%, 98% or 99% identical to the nucleic acid sequence shown in FIGS. 1A–1B or to the nucleic acid sequence of the deposited cDNA which do, in fact, encode a polypeptide having CD44-like protein activity. By "a polypeptide having CD44-like protein activity" is intended polypeptides exhibiting similar, but not necessarily identical, activity as compared to the CD44-like protein as measured in a particular biological assay.

For example, it is known that CD44 and fragments thereof are capable of inhibiting T cell receptor-mediated T cell activation (Denning et al., *Immunol* 798–801 (1989); Shimazu et al. *J. Immunol.* 143:2457–2463 (1989); WO 94/09811). Briefly, the assay involves assessing the effect of soluble CD44-like protein on T cell activation by incorporating affinity purified CD44-like protein into liposomes, incubating the liposomes with peripheral blood mononuclear cells prior to stimulation with CD2 antibodies (which are potent stimulators of T cell activation). As it is believed that the CD44-like protein of the present invention will significantly decrease T-cell proliferation when added to T cells immediately before the addition of CD2 antibodies, it will thus be possible to determine whether a candidate polypeptide has CD44-like protein activity.

As another example, CD44 is known to act as a receptor for hyaluronan, and is thus proposed to be important for cell-extracelluar matrix interaction. A hyaluronan binding assay is described in Telen et al., *J. Biol. Chem.* 271:7147–7153 (1996) and in WO 94/09811. Briefly the assay involves contacting either (1) cells which express CD44 on their surface or (2) cells which do not express CD44 with hyaluronan that has been labeled with FITC, washing the cells, resuspending the cells in PBS containing 0.3% paraformaldehyde, and analyzing the cells for FITC labeling by flow cytometry. Like CD44, the CD44-like protein of the present invention will bind hyaluronan. Thus, by the invention, a "polypeptide having CD44-like protein activity" includes polypeptides that are capable of specific binding of hyaluronan.

Of course, due to the degeneracy of the genetic code, one of ordinary skill in the art will immediately recognize that large number of the nucleic acid molecules at least 95%, 96%, 97%, 98% or 99% identical to the nucleic acid sequence of the deposited cDNA or the nucleic acid sequence shown in FIGS. 1A–1B [SEQ ID NO:1] will encode a polypeptide "having CD44-like protein activity." In fact, since degenerate variants all encode the same polypeptide, this will be clear to the skilled artisan even without performing the above described comparison assay. It will be further recognized in the art that, for such nucleic acid molecules that are not degenerate variants, a reasonable number will also encode a polypeptide having CD44-like protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra, and the references cited therein.

Vectors and Host Cells

The present invention also relates to vectors which include the isolated DNA molecules of the present invention, host cells which are genetically engineered with the recombinant vectors, and the production of CD44-like polypeptides or fragments thereof by recombinant techniques.

Recombinant constructs may be introduced into host cells using well known techniques such as infection, transduction, transfection, transvection and transformation. The vector may be, for example, a plasmid, plasmid, viral or retroviral vector. Retroviral vectors may be replication competent or replication defective. In the latter case, retroviral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transfected into host cells.

Preferred are vectors comprising cis-acting control regions to the polynucleotide of interest. Appropriate transacting factors either are supplied by the host, supplied by a complementing vector or supplied by the vector itself upon introduction into the host.

In certain preferred embodiments in this regard, the vectors provide for specific expression, which may be inducible and/or cell type-specific. Particularly preferred among inducible vectors are vectors that can be induced for expression by environmental factors that are easy to manipulate, such as temperature and nutrient additives.

Expression vectors useful in the present invention include chromosomal-, episomal- and virus-derived vectors e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably contain selectable markers. Such markers include dihydrofolate reductase or neomycin resistance for eukaryotic cell culture and tetracycline or ampicillin resistance for culturing in E. coli and other bacteria. Representative examples of appropriate hosts include bacterial cells, such as E. coli, Streptomyces and Salmonella typhimurium; fungal cells, such as yeast; insect cells such as Drosophila S2 and Spodoptera Sf9; animal cells such as CHO, COS and Bowes melanoma; and plant cells. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters for use in the present invention include E. coli lacI and lacZ promoters, the T3 and T7 promoters, the gpt promoter, the lambda PR, PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

The CD44-like protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

CD44-Like Polypeptides and Fragments

The invention further provides an isolated CD44-like polypeptide having the amino acid sequence encoded by the deposited cDNA, or the amino acid sequence as shown in FIGS. 1A–1B [SEQ ID NO:2], or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequence of the CD44-like polypeptide can be varied without significant effect of the structure or function of the protein. If such differences in sequence are contemplated, it should be remembered that there will be critical areas on the protein which determine activity. Such areas may comprise residues which make up the extra cellular domain. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the CD44-like polypeptide which show substantial CD44-like polypeptide activity or which include regions of CD44-like protein such as the protein fragments discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the CD44-like polypeptide. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the CD44-like polypeptide of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the CD44-like protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention are preferably provided in an isolated form. By "isolated" polypeptide is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the CD44-like protein can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids from about –21 to about 301 in SEQ ID NO:2; a polypeptide comprising amino acids from about –2 0 to about 301 in SEQ ID NO:2; a polypeptide comprising amino acids from about 1 to about 301 in SEQ ID NO:2; a polypeptide comprising amino acids from about 1 to about 217 in SEQ ID NO:2; a polypeptide comprising amino acids from about 218 to about 245 in SEQ ID NO:2; a polypeptide comprising amino acids from about 246 to about 301 in SEQ ID NO:2; a polypeptide comprising the CD44-like polypeptide extracellular and intracellular domains with all or part of the transmembrane domain deleted; as well as polypeptides at least 95% identical, more preferably at least 96% identical, still more preferably at least 97%, 98% or 99% identical to the polypeptide encoded by the deposited cDNA, to the polypeptide of SEQ ID NO:2, and also include portions of such polypeptides with at least 30 amino acids and more preferably at least 50 amino acids.

By a polypeptide having an amino acid sequence at least, for example, 95% "identical" to a reference amino acid sequence of a CD44-like polypeptide is intended that the amino acid sequence of the polypeptide is identical to the reference sequence except that the polypeptide sequence may include up to five amino acid alterations per each 100 amino acids of the reference amino acid of the CD44s-like polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIGS. 1A–1B [SEQ ID NO:2] or to the amino acid sequence encoded by deposited cDNA clone or a portion thereof can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998–4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660–666 (1984). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A., et al., *Cell* 37:767–778 at 777 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A., *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present inventors have discovered that the CD44-like polypeptide is a 322 residue protein exhibiting three main structural domains. First, the extracellular domain (which includes the ligand binding domain) was identified within residues from about 22 to about 238 in FIGS. 1A–1B [residues from about 1 to about 217 SEQ ID NO:2]. The mature extracellular domain has been predicted by the inventors as being about 216 amino acids in length with a molecular weight of about 23.5 kDa. Second, the transmembrane domain was identified within residues from about 239 to about 266 in FIGS. 1A–1B [residues from about 218 to about 245 SEQ ID NO:2]. Third, the intracellular domain was identified within residues from about 267 to about 322 in FIGS. 1A–1B [residues from about 246 to about 301 SEQ ID NO:2].

Thus, the invention further provides preferred CD44-like protein fragments comprising a polypeptide selected from: the mature CD44-like protein; the CD44-like polypeptide extracellular domain; the CD44-like polypeptide transmembrane domain; the CD44-like polypeptide intracellular domain; or the CD44-like protein extracellular domain and intracellular domain with part or all of the transmembrane domain deleted. Methods for producing such CD44-like protein fragments are described above.

As indicated above, the extracellular domain of the CD44-like receptor of the present invention can be combined with parts of the constant domain of immunoglobulins (IgG), resulting in chimeric polypeptides. These fusion proteins show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing the ligands that the monomeric extracellular domains alone (Fountoulakis et al., J Biochem 270:3958–3964 (1995)).

As described in detail below, the polypeptides of the present invention and fragments thereof can be used to raise polyclonal and monoclonal antibodies, which are useful in diagnostic assays for detecting CD44-like protein expression as described below or as agonists and antagonists capable of enhancing or inhibiting the CD44-like protein receptor signaling pathway. Further, such fragments can be used in the yeast two-hybrid system to "capture" CD44-like protein binding proteins which are also candidate agonist and antagonist according to the present invention. The yeast two hybrid system, which is discussed in more detail below, is described in Fields and Song, Nature 340:245–246 (1989). Further, the extracellular domain in soluble form is itself useful as an antagonist capable of inhibiting CD44-like protein signaling.

The entire disclosure of each document cited in this section on "CD44-Like Polypeptides and Fragments" is hereby incorporated herein by reference.

Cancer Diagnosis and Prognosis

It is believed that certain tissues in mammals with cancer contain significantly greater CD44-like protein gene copy number and express significantly enhanced levels of the CD44-like protein and mRNA encoding the CD44-like protein when compared to a corresponding "standard" mammal, i.e., a mammal of the same species not having the cancer. Further, enhanced levels of the CD44-like protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the CD44-like protein or the gene copy number in mammalian cells or body fluid and comparing the gene expression level or gene copy number with a standard CD44-like protein gene expression level or gene copy number, whereby an increase in the gene expression level or gene copy number over the standard is indicative of certain tumors.

Where a tumor diagnosis has already been made according to conventional methods, the present invention is useful as a prognostic indicator, whereby patients exhibiting enhanced CD44-like protein gene expression will experience a worse clinical outcome relative to patients expressing the gene at a lower level.

By "assaying the expression level of the gene encoding the CD44-like protein" is intended qualitatively or quantitatively measuring or estimating the level of the CD44-like protein or the level of the mRNA encoding the CD44-like protein in a first biological sample either directly (e.g., by determining or estimating absolute protein level or mRNA level) or relatively (e.g., by comparing to the CD44-like protein level or mRNA level in a second biological sample). By "assaying the copy number of the gene encoding the CD44-like protein" is intended qualitatively or quantitatively measuring or estimating the gene copy number in a first biological sample either directly (e.g., by determining or estimating absolute gene copy number) or relatively (e.g., by comparing to the CD44-like protein gene copy number in a second biological sample).

Preferably, the CD44-like protein level, mRNA level, or gene copy number in the first biological sample is measured or estimated and compared to a standard CD44-like protein level, mRNA level, or gene copy number, the standard being taken from a second biological sample obtained from an individual not having the cancer. As will be appreciated in the art, once a standard CD44-like protein level, mRNA level, or gene copy number is known, it can be used repeatedly as a standard for comparison.

By "biological sample" is intended any biological sample obtained from an individual, cell line, tissue culture, or other source which contains CD44-like protein or mRNA. Biological samples include mammalian body fluids (such as sera, plasma, urine, and spinal fluid) which contain secreted mature CD44-like protein or its soluble extracellular domain, and ovarian, prostate, heart, placenta, pancreas liver, spleen, lung, breast and umbilical tissue. Other biological samples include bone marrow. Methods for obtaining tissue biopsies and body fluids from mammals are well known in the art. Where the biological sample is to include mRNA, a tissue biopsy is the preferred source.

The present invention is useful for detecting cancer in mammals. In particular the invention is useful during diagnosis of the of following types of cancers in mammals: breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenolchloroform method described in Chomczynski and Sacchi, *Anal. Biochem.* 162:156–159 (1987). Levels of mRNA encoding the CD44-like protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. CD44-like protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the CD44-like protein). Northern blot analysis can be performed as described above.

Preferably, levels of mRNA encoding the CD44-like protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the CD44-like protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying CD44-like protein gene copy number can occur according to any known technique, such as for example, in situ hybridization of tissue samples with a cDNA probe described above.

Assaying CD44-like protein levels in a biological sample can occur using any art-known method. Preferred for assaying CD44-like protein levels in a biological sample are antibody-based techniques. For example, CD44-like protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of CD44-like protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of CD44-like protein can be accomplished using isolated CD44-like protein as a standard. This technique can also be applied to body fluids. With these samples, a molar concentration of CD44-like protein will aid to set standard values of CD44-like protein content for different body fluids, like serum, plasma, urine, spinal fluid, etc. The normal appearance of CD44-like protein amounts can then be set using values from healthy individuals, which can be compared to those obtained from a test subject.

Other antibody-based methods useful for detecting CD44-like protein gene expression include immunoassays, such as the enzyme linked immunosorbent assay (ELISA) and the radioimmunoassay (RIA). For example, a CD44-like protein-specific monoclonal antibodies can be used both as an immunoabsorbent and as an enzyme-labeled probe to detect and quantify the CD44-like protein. The amount of CD44-like protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect CD44-like protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting CD44-like protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur (35S), tritium ($^{3}$H), indium ($^{112}$In), and technetium ($^{99m}$Tc), and fluorescent labels, such as fluorescein and rhodamine, and biotin.

In addition to assaying CD44-like protein levels in a biological sample obtained from an individual, CD44-like protein can also be detected in vivo by imaging. Antibody labels or markers for in vivo imaging of CD44-like protein include those detectable by X-radiography, NMR or ESR. For X-radiography, suitable labels include radioisotopes such as barium or caesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CD44-like protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain CD44-like protein. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer*, eds., S. W. Burchiel and B. A. Rhodes, Masson Publishing Inc. (1982)).

CD44-like-protein specific antibodies for use in the present invention can be raised against the intact CD44-like protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (mAb) is meant to include intact molecules as well as antibody fragments (such as, for example, Fab and F(ab')$_2$ fragments) which are capable of specifically binding to CD44-like protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the CD44-like protein or an antigenic fragment thereof can be administered to an animal in order to induce the production of sera containing polyclonal antibodies. In a preferred method, a preparation of CD44-like protein is prepared and purified to render it substantially free of natural contaminants. Such apreparation is then introduced into an animal in order to produce polyclonal antisera of greater specific activity.

In the most preferred method, the antibodies of the present invention are monoclonal antibodies (or CD44-like protein binding fragments thereof). Such monoclonal antibodies can be prepared using hybridoma technology (Kohler et al., *Nature* 256:495 (1975); Kohler et al.,*Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N.Y., pp. 563–681 (1981)). In general, such procedures involve immunizing an animal (preferably a mouse) with a CD44-like protein antigen or, more preferably, with a CD44-like protein-expressing cell. Suitable cells can be recognized by their capacity to bind anti-CD44-like protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the CD44-like protein antigen.

Alternatively, additional antibodies capable of binding to the CD44-like protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CD44-like-protein specific antibodies are used to immunize an animal, preferably a mouse. The splenocytes of such an animal are then used to produce hybridoma cells, and the hybridoma cells are screened to identify clones which produce an antibody whose ability to bind to the CD44-like protein-specific antibody can be blocked by the CD44-like protein antigen. Such antibodies comprise anti-idiotypic antibodies to the CD44-like protein-specific antibody and can be used to immunize an animal to induce formation of further CD44-like protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, CD44-like protein-binding fragments can be produced through the application of recombinant DNA technology or through synthetic chemistry.

Where in vivo imaging is used to detect enhanced levels of CD44-like protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the CD44-like protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med* 10:296–301 (1985); Carasquillo et al., *J. Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:140 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Therapeutics and Screening Assays

CD44 is a broadly distributed cell surface glycoprotein that has been shown to play an important role in many adhesion-dependent cellular processes including lymphocyte recirculation, hemopoiesis, NK-cell mediated killing, macrophage and lymphocyte activation, and tumor metastasis (Telen et al., *J. Biol. Chem.* 271(12): 7147–7153 (1996)). CD44 is known to function as a receptor for the glycosaminoglycan hyaluronan, which has been associated with wound repair, tumor invasion and immune recognition (Yang et al., *J. Biol. Chem.* 268(12):8617–8623 (1993)). However, it is becoming increasingly clear that not all CD44-dependent adhesion events involve recognition of this particular ligand. CD44 has been shown to be capable of binding a number of extracellular matrix components besides hyaluronan, such as fibronectin, heparin sulfate, collagen types I and VI, and chondroitin 4- and 6-sulfates (Aruffo et al., *Cell* 61:1303–1313 (1990)). Another ligand of CD44 is the cytokine osteopontin, which interacts with CD44 surface receptors to induce cell migration (Biocentury, Jan 29, 1996 referencing Science).

CD44 is a very polymorphic molecule; species ranging in size from 80 to 250 kDa have been detected on various normal and transformed cell types. Some of this heterogeneity can be attributed to post-translational modification of a common polypeptide core. However, it has also been demonstrated that the 10 contiguous exons of a single copy of the gene for CD44 can be alternatively spliced, generating higher molecular mass CD44 isoforms that contain additional peptide sequences of varying length inserted into a single site within the extracellular domain of the molecule proximal to the membrane spanning domain. Furthermore, several recent studies ascribe unique functional activities to certain of these isoforms. This may indicate that the ligand-binding specificity can be altered by the inclusion of extra peptide sequences within the extracellular domain of CD44.

The various cellular responses in which CD44 is involved are induced by the binding of a CD44 ligand to a CD44 receptor, including the CD44-like receptor protein of the present invention. Cells which express the CD44-like receptor, and which are likely to have a potent cellular response to ligands of the CD44-like receptor, include hematopoietic cells and lymphocytes. By a "cellular response to ligands of the CD44-like receptor" is intended any genotypic, phenotypic and/or morphologic change to a cell, cell line, tissue, tissue culture or patient that is induced by such a ligand.

Thus, one aspect of the present invention is directed to the identification of compounds capable of binding to the CD44-like protein of the invention. As it is believed that the CD44-like protein of the present invention is capable of binding to hyaluronan, new ligands of the CD44-like protein can be identified by their ability to interfere with the binding of labeled hyaluronan to the CD44-like protein of the invention. An assay which may be utilized to determine hyaluronan binding is disclosed in Telen, et al., *J. Biol. Chem.* 271:7147–7153 (1996). Briefly, this method involves comparing the degree to which FITC-hyaluronan binds to cells expressing the CD44-like protein of the invention, as measured by flow cytometry, to the degree to which the same cells bind FITC-hyaluronan when the cells are first incubated with a solution containing a proposed ligand of the CD44-like molecule.

In another aspect, the present invention is directed to a method for enhancing a cellular response induced by the CD44-like protein-mediated signaling pathway, which involves administering to a cell which expresses the CD44-like protein an effective amount of an agonist to enhance CD44-like protein-mediated signaling.

In a further aspect, the present invention is directed to a method for inhibiting a cellular response induced by the CD44-like protein-mediated signaling pathway, which involves administering to a cell which expresses the CD44-like protein an effective amount of an antagonist capable of inhibiting CD44-like protein-mediated signaling. Preferably, CD44-like protein-mediated signaling is inhibited to treat metastasis. An example of an antagonist capable of diminishing CD44-mediated cell migration is hyaluronate (Biocentury, Jan 29, 1996). In a further preferred embodiment, CD44-like protein mediated signaling is decreased to inhibit graft versus host disease.

By "agonist" is intended naturally occurring and synthetic compounds capable of enhancing or potentiating a cellular response to a ligand of the CD44-like protein. By "antagonist" is intended naturally occurring and synthetic compounds capable of inhibiting a cellular response to a CD44-like ligand. Whether any candidate "agonist" or "antagonist" of the present invention can enhance or inhibit such a cellular response can be determined using art-known CD44-like protein ligand/receptor cellular response or binding assays, including those described in more detail below.

One method involves screening for compounds which inhibit activation of the receptor polypeptide of the present invention by determining inhibition of binding of labeled ligand to cells which have the receptor on the surface thereof. Such a method involves transfecting a eukaryotic cell with DNA encoding the CD44-like protein receptor such that the cell expresses the receptor on its surface and contacting the cell with a candidate compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

In a further aspect, a screening method is provided for determining whether a candidate agonist or antagonist is capable of enhancing or inhibiting a cellular response induced by the CD44-like receptor pathway. The method involves contacting cells which express the CD44-like protein polypeptide with a candidate compound, assaying a cellular response, and comparing the cellular response to a standard cellular response, the standard being assayed in the absence of the candidate compound, whereby an increased cellular response over the standard indicates that the candidate compound is an agonist of the CD44-like protein receptor signaling pathway and a decreased cellular response compared to the standard indicates that the candidate compound is an antagonist of the CD44-like protein receptor signaling pathway. By "assaying a cellular response" is intended qualitatively or quantitatively measuring a cellular response to a candidate compound and/or a CD44-like protein ligand. By the invention, a cell expressing the CD44-like protein polypeptide can be contacted with either an endogenous or exogenously administered CD44 ligand.

Another specific example of such an assay will allow the identification of compounds capable of inhibiting smooth muscle cell migration mediated by the CD44-like protein of the invention. The assay includes the steps of providing a smooth muscle cell bearing the CD44-like molecule on its surface, contacting the smooth muscle cell with a candidate compound, and determining the amount of smooth muscle migration that occurs. A decrease in migration of the smooth muscle cell in the presence of a candidate compound compared to the amount in the absence of the candidate compound indicates that the candidate compound inhibits smooth muscle migration that is mediated by the CD44-like molecule. This assay is described in more detail in WO 95/19183 and Jain et al., *J. Clin. Invest.* 97(3):596–603 (1996).

Agonists according to the present invention include naturally occurring and synthetic compounds such as, for example, CD44 ligands and fragments thereof. Other preferred agonist includes polyclonal and monoclonal antibodies raised against the CD44-like receptor polypeptide, or a fragment thereof. Such agonist antibodies can be raised against the CD44-like protein as described in WO 95/2224913, WO 93/17047, and Moll et al., *Journal of Immunology* 2085–2094.

Antagonists according to the present invention include naturally occurring and synthetic compounds such as, for example, the cytokine osteopontin (Weber et al., *Science* 271:509–512 (1996)). Other antagonists include polyclonal and monoclonal antagonist antibodies raised against the CD44-like protein or a fragment thereof.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); OLIGODEOXYNUCLEOTIDES AS ANTISENSE INHIBITORS OF GENE EXPRESSION, CRC Press, Boca Raton, Fla. (1988). Triple helix formation is discussed in, for instance Lee et al., *Nucleic Acids Research* 6:3073 (1979); Cooney et al., *Sci-* ence 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonists according to the present invention include soluble forms of CD44-like protein, e.g., CD44-like protein fragments that include the extracellular domain, which contains the ligand binding region. Such soluble forms of the receptor, which may be naturally occurring or synthetic, antagonize CD44-like protein-mediated signaling by competing with the cell surface CD44-like protein receptor for binding to CD44 receptor ligands.

The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of methods using CD44-like protein immunogens of the present invention. As indicated, such CD44-like protein immunogens include the full length CD44-like protein polypeptide (which may or may not include the leader sequence) and CD44-like protein polypeptide fragments such as the extracellular domain, the transmembrane domain, and the intracellular domain.

In a preferred method, antibodies according to the present invention are mAbs. Such mAbs can be prepared using hybridoma technology as described above and in the following references: Kohler and Millstein, *Nature* 256:495–497 (1975) and U.S. Pat. No. 4,376,110; Harlow et al, *Antibodies: A Laboratory Manual,* Cold Spring Harbor Laboratory Press, Cold Spring Harbor, N.Y., 1988; *Monoclonal Antibodies and Hybridomas: A New Dimension in Biological Analyses,* Plenum Press, New York, N.Y., 1980; Campbell, "Monoclonal Antibody Technology," In: *Laboratory Techniques in Biochemistry and Molecular Biology,* Volume 13 (Burdon et al., eds.), Elsevier, Amsterdam (1984).

Also intended within the scope of the present invention are humanized chimeric antibodies, produced using genetic constructs derived from hybridoma cells producing the mAbs described above. Methods for production of chimeric antibodies are known in the art. See, for review: Morrison, *Science,* 229:1202–1207 (1985); Oi et al., *BioTechniques* 4:214 (1986); see, also: Cabilly et al., U.S. Pat. No. 4,816,567 (Mar. 28, 1989); Taniguchi et al, EPO Patent Public. EP171496 (Feb. 19, 1986); Morrison et al., EPO Patent Pub. EP173494 (Mar. 5, 1986); Neuberger et al, PCT Pub. WO8601533 (Mar. 13, 1986); Robinson et al., PCT Pub. WO 8702671 (May 7, 1987); Boulianne et al., *Nature* 312:643–646 (1984); Neuberger et al, *Nature* 314:268–270 (1985).

Proteins and other compounds which bind the CD44-like protein domains are also candidate agonist and antagonist according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (Gyuris, J. et al., *Cell* 75:791–803 (1993); Zervos, A. S. et al, *Cell* 72:223–232 (1993)). Briefly, a domain of the CD44-like protein polypeptide is used as bait for binding compounds. Positives are then selected by their ability to grow on plates lacking leucine, and then further tested for their ability to turn blue on plates with X-gal, as previously described in great detail (Gyuris, J. et al., *Cell* 75:791–803 (1993)). Preferably, the yeast two-hybrid system is used according to the present invention to capture compounds which bind to either the CD44-like protein ligand binding domain or to the CD44-like protein intracellular domain. Such compounds are good candidate agonist and antagonist of the present invention. This system has been used previously to isolate proteins which bind to the intracellular domain of the p55 and p75 TNF receptors (WO 95/31544).

By a "CD44-like protein receptor ligand" is intended naturally occurring, recombinant, and synthetic ligands that are capable of binding to the CD44-like protein receptor and inducing the receptor signaling pathway. Examples of ligands of the CD44-like protein receptor include, but are not limited to, hyaluronate and osteopontin.

Therapeutic uses involving the CD44-like protein receptor of the present invention include treatment or prevention of tissue necrosis, thermal injury, scarring, arteriosclerosis, vascular restenosis, inflammation, graft versus host disease, cancer, and metastasis. More detail related to these representative therapeutic applications of the present invention is given below.

One therapeutic use involving the CD44-like protein of the invention is a method for treating tissue necrosis, or loss, in an animal. Tissue necrosis is treated by providing the subject with a therapeutically effective amount of an antagonist of the CD44-like molecule of the invention, where the CD44-like molecule is expressed on the surface of inflammatory cells or endothelial cells. The antagonist will contain the progression of tissue injury by preventing the influx of neutrophils, especially polymorphonuclear neutrophils (which are inflammatory cells) to a burn site. Thus, a preferred application of this method will be in the treatment and containment of tissue necrosis surrounding a burn injury, such as a thermal injury resulting from skin contact with elevated temperatures, such as a heated stove, etc. The treatment with the agent capable of binding the CD44-like molecule of the invention should begin with measuring the tissue necrosis within one hour of a burn to provide a reference point of the burn size, treating the animal with a therapeutic amount of the agent, continuing to treat the animal with the agent for not more than 24 hours after the burn contact, and measuring the tissue necrosis after the treatment, wherein a treated size equal to the reference size indicates an inhibition of the progression of tissue necrosis (WO 93/17047). Modes of administration and dosages are discussed in detail below.

The above method for the treatment of thermal injury may also be effective for decreasing scarring or the formation of scar tissue attendant the healing process at a burn site. As is used herein, scarring is defined as the formation of fibrous tissue at sites where normal tissue has been destroyed. The present invention thus also includes a method for decreasing scarring specifically at skin tissue areas of second or third degree burn. This method comprises treating an animal with a second or third degree burn with a therapeutically effective amount of a pharmaceutically acceptable preparation comprising an antagonist of the CD44-like molecule of the invention to decrease tissue scarring in an animal. Such an agent can of course include an antibody capable of binding the CD44-like molecule of the invention.

Another therapeutic use involving the CD44-like molecule of the invention is a method for treating arteriosclerosis (the abnormal hardening or thickening of arterial walls) or vascular restenosis (the narrowing or constriction of blood vessel walls) in an animal by inhibiting smooth muscle migration or proliferation that is mediated by the CD44-like protein receptor of the invention. Thus, the method comprises inhibiting expression of the CD44-like molecule of the invention by introducing into the target cells of the patient by standard vectors and/or gene delivery systems, a therapeutically effective amount of an isolated antisense DNA of the CD44-like molecule. Suitable gene delivery systems may include liposomes, receptor-mediated delivery systems, naked DNA, and viral vectors such as herpes viruses, retroviruses and adenoviruses, among others.

Yet another method of treatment included in the present invention comprises a method for treating graft-versus-host disease (GvHD). One of the complications that may arise in tissue transplantation involves an immune response mounted by the graft tissue against the host. This is the principle complication involved in the use of lymphoid tissue in transplantation therapies, particularly bone marrow transplants (WO 95/24913). Thus, one aspect of the present invention is directed to administering to the recipient of a tissue transplant, preferably during a time period concurrent with the presence of a transplant, a therapeutic amount of a preparation comprising an antagonist of the CD44-like protein receptor. In another embodiment, the donor tissue is exposed to the above-described pharmaceutical preparation prior to transplant for a period of time sufficient to inhibit or prevent a graft-versus-host response upon implantation (WO 95/24913).

Another therapeutic use included in the invention is a method of treating inflammation or inhibiting cancer cell metastasis. CD44 is known to be a proinflammatory molecule involved in immune cell activation (reviewed in Haynes et al., *Immunol. Today* 10:423–428 (1989)) as well as metastasis of certain tumor cell types (Id., WO 94/09811). The CD44 molecule has been shown to be upregulated in rheumatoid arthritis on many synovial cell types; the level of CD44 present in synovial tissue is directly proportional to the degree of synovial inflammation.

Thus, the present invention includes a method of treating inflammation in an animal comprising administering to the animal a therapeutically effective amount of an antagonist of the CD44-like protein of the invention, or a fragment thereof, in an amount sufficient to reduce the inflammation.

In another embodiment, the invention relates to a method of transporting a drug or cytotoxic agent to a site of inflammation in an animal, comprising administering to the animal an anti-CD44-like protein monoclonal antibody linked to a drug or cytotoxic agent. In a preferred embodiment, the monoclonal antibody and the drug or cytotoxic agent (which, together, are referred to as an immunotoxin) are incorporated into a liposome for delivery to the site of inflammation.

A similar principle can be utilized in order to prevent metastasis. The process of metastatic spread of tumor cells requires interactions between the tumor cells and the stromal cells, as well as recognition by cell surface receptors of the tumor cells of ligands comprising the extracellular matrix. As CD44 is one of the receptors found to be expressed at high levels in tumor tissue, and as the CD44 ligand hyaluronate, which induces homotypic aggregation, is present in the extracellular matrix, it follows that the administration of an antagonist of the CD44-like protein would inhibit the interaction between CD44 and hyaluronate that occurs in metastasis (Weber et al., *Science* 271:509–512 (1996)).

Therefore, in another embodiment, the present invention relates to a method of inhibiting binding of hyaluronan to the CD44-like molecule of the invention, comprising contacting the CD44-like molecule with a therapeutically effective amount of an antagonist under conditions such that binding of hyaluronan to the CD44-like molecule is inhibited.

Yet another therapeutic method included in the invention is a method of treating cancer by administering to an animal suffering from cancer a pharmaceutically effective amount of an antagonist compound capable of binding to cancer cells, wherein the compound is associated with a substance capable of damaging cancer cells.

The agonist or antagonist described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a CD44-like protein receptor ligand. One of ordinary skill will appreciate that effective amounts of an agonist or antagonist can be determined empirically and may be employed in pure form or, where such forms exist, in pharmaceutically acceptable salt, ester or prodrug form. The agonist or antagonist my be administered in compositions in combination with one or more pharmaceutically acceptable excipients. It will be understood that, when administered to a human patient, the total daily usage of the compounds and compositions of the present invention will be decided by the attending physician within the scope of sound medical judgement. The specific therapeutically effective dose level for any particular patient will depend upon a variety of factors including the type and degree of the cellular response to be achieved; activity of the specific agonist or antagonist employed; the specific composition employed; the age, body weight, general health, sex and diet of the patient; the time of administration, route of administration, and rate of excretion of the agonist or antagonist; the duration of the treatment; drugs used in combination or coincidental with the specific agonist or antagonist; and like factors well known in the medical arts.

For example, satisfactory results are obtained by oral administration of a antagonist or agonist at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

From above, pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a CD44-like receptor ligand, clinical side effects can be reduced by using lower doses of both the ligand and the agonist. It will be understood that the agonist can be "co-administered" either before, after, or simultaneously with the CD44-like receptor ligand, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the agonist or antagonist, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelullose, alginates, gelatin, polyvinylpyrrolidone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredient in finely divided form may be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the agonist or antagonist with suitable non-irritating excipients or carriers such as cocoa butter, polyethylene glycol or a suppository wax which are solid at room temperature but liquid at body temperature and therefore melt in the rectum or vaginal cavity and release the drugs.

The agonist or antagonist can also be administered in the form of liposomes. As is known in the art, liposomes are generally derived from phospholipids or other lipid substances. Liposomes are formed by mono- or multi-lameflar hydrated liquid crystals that are dispersed in an aqueous medium. Any non-toxic, physiologically acceptable and metabolizable lipid capable of forming liposomes can be used. The present compositions in liposome form can contain, in addition to the agonist or antagonist, stabilizers, preservatives, excipients, and the like. The preferred lipids are the phospholipids and the phosphatidyl choaes (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Having generally described the invention, the same will more readily be understood by reference to the following examples, which are provided by way of illustration and are not intended as limiting.

EXAMPLES

Example 1

Expression in *E. coli*

The DNA sequence encoding the CD44-like protein in the deposited polynucleotide is amplified using PCR oligonucleotide primers specific to the amino acid carboxyl terminal sequence of the CD44-like protein and to vector sequences 3' to the gene. Additional nucleotides containing restriction sites to facilitate cloning are added to the 5' and 3' sequences respectively.

The 5' oligonucleotide primer has the sequence:

5' CGCCCATGGTCCAAGGCTCTTTGCGT 3' [SEQ ID NO:4], containing the underlined NcoI restriction site, which encodes a start ATG within the NcoI site.

The 3' primer has the sequence:

5' CGCAAGCTTTCAAGCCGTGGGGACACCTC 3' [SEQ ID NO:5], containing the underlined Hind III restriction site.

The restrictions sites are convenient to restriction enzyme sites in the bacterial expression vector pQE-60, which is used for bacterial expression in these examples. (Qiagen, Inc. 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified CD44-like protein DNA and the vector pQE60 both are digested with NcoI and Hind III and the digested DNAs are then ligated together. Insertion of the CD44-like protein DNA into pQE60 places the CD44-like protein coding region downstream of and operably linked to the vector's IPTG-inducible promoter, and in-frame with an initiating AUG appropriately positioned for translation of the CD44-like protein.

The ligation mixture is transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the illustrative example described here. This strain, which is only one of many that are suitable for expressing the CD44-like protein, is available commercially from Qiagen.

Transformants are identified by their ability to grow on LB plates in the presence of ampicillin. Plasmid DNA is isolated from resistant colonies and the identity of the cloned DNA is confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells are then harvested by centrifugation and disrupted, by standard methods. Inclusion bodies are purified from the disrupted cells using routine collection techniques, and protein is solubilized from the inclusion bodies into 8 M urea. The 8 M urea solution containing the solubilized protein is passed over a PD-10 column in 2X phosphate buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2X PBS at a concentration of 95 micrograms per mL.

Example 2

Expression in Mammalian Cells (CHO, COS and Others).

Most of the vectors used for the transient expression of the CD44-like protein gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, also cellular signals can be used (e.g. human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1 African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Using this marker, the mammalian cells are grown in increasing amounts of methotrexate for selection and the cells with the highest resistance are selected These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–4470 (March, 1985)) plus a fragment of the CMV-enhancer (Boshart et al., *Cell* 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 24

Expression of Extracellular Soluble Domain of CD44-like Protein in COS Cells

The expression plasmid, CD44-like protein HA, is made by cloning a cDNA encoding CD44-like protein into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire CD44-like protein precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows.

The CD44-like protein cDNA of the deposit clone is amplified using primers that contained convenient restriction sites, much as described above regarding the construction of expression vectors for expression of CD44-like protein in *E. coli* and *S. fugiperda*.

To facilitate detection, purification and characterization of the expressed CD44-like protein, one of the primers contains a hemagglutinin tag ("HA tag") as described above.

Suitable primers include that following, which are used in this example; the 5' primer CGC GGA TCC GCC ATC ATG GCC AGG TGC TTC AGC 3' [SEQ ID NO:6] contains the underlined Bam HI site, an ATG start codon and 15 codons thereafter.

For the extracellular domain the 3' primer, containing the underlined XbaI site, stop codon, hemagglutinin tag and last 15 bp preceding transmembrane domain (at the 3' end) has the following sequence: 5' CGC TCT AGA TCA AGC GTA GTC TGG GAC GTC GTA TGG GTA AGC CTG GGG GAC ACC TC 3' [SEQ ID NO:7].

The PCR amplified DNA fragment and the vector, pcDNAI/Amp, are digested with Bam HI and Xba I and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the CD44-like protein-encoding fragment.

For expression of recombinant CD44-like protein, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of CD44-like protein by the vector.

Expression of the CD44-like protein HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 2B

Expression and Purification of Human CD44-like Protein Using the CHO Expression System The DNA sequence encoding CD44-like protein in the deposited polynucleotide is amplified using PCR oligonucleotide primers specific to the carboxyl terminal sequence of the CD44-like protein and to vector sequences 3' to the gene. Additional nucleotides containing restriction sites to facilitate cloning are added to the 5' and 3' sequences respectively.

For both the full length gene and the nucleotide sequence encoding the extracellular soluble domain, the 5' primer has the sequence 5' CGC GGA TCC GCC ATC ATG GCC AGG TGC TTC AGC 3' [SEQ ID NO:9] containing the underlined Bam HI restriction enzyme site followed by Kozak sequence and 18 bases of the sequence of CD44-like protein receptor of FIGS. 1A–1B. For the full length gene the 3' primer has the fill length sequence CGC GGT ACC TCA ACC AGC CTC AGG TGT 3' [SEQ ID NO:8], containing the underlined Asp718 restriction followed by nucleotides complementary to 18 bp preceding the transmembrane domain of the CD44-like protein receptor set out in FIGS. 1A–1B, including the stop codon. For the extracelluar domain the 3' primer has the sequence of 5' CGC GGT ACC TCA AGC CGT GGG GAC ACC TC 3' [SEQ ID NO:10], containing the underlined Asp718 restriction followed by nucleotides complementary to 18 bp preceding the stop codon of the CD44-like protein receptor set out in FIGS. 1A–1B, including the stop codon.

The restrictions sites are convenient to restriction enzyme sites in the CHO expression vectors PC4.

The amplified CD44-like protein DNA and the vector PC4 both are digested with BamHI and the digested DNAs then ligated together. Insertion of the CD44-like protein DNA into the BamHI restricted vector placed the CD44-like protein coding region downstream of and operably linked to the vector's promoter. The ligation mixture is transformed into competent E. coli cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989).

Example 3

Cloning and Expression of the Soluble Extracellular Domain of CD44-like Protein in a Baculovirus Expression System The cDNA sequences encoding either the soluble extracellular domain or the full length protein of the CD44-like protein receptor protein in the deposited clone is amplified using PCR oligonucleotide primers corresponding to the 5' and 3' sequences of the gene:

The 5' primer for expression of either the extracellular domain or the full length protein has the sequence 5' CGC GGA TCC GCC ATC ATG GCC AGG TGC TTC AGC 3' [SEQ ID NO:9] containing the underlined Bam HI restriction enzyme site followed by Kozak sequence and 18 bases of the sequence of CD44-like protein receptor of FIGS. 1A–1B. Inserted into an expression vector, as described below, the 5' end of the amplified fragment encoding CD44-like protein receptor provides an efficient signal peptide. An efficient signal for initiation of translation in eukaryotic cells, as described by Kozak, M., *J. Mol. Biol.* 196: 947–950 (1987) is appropriately located in the vector portion of the construct.

For the full length gene the 3' primer has the full length sequence CGC GGT ACC TCA ACC AGC CTC AGG TGT [SEQ ID NO:8], containing the underlined Asp718 restriction followed by nucleotides complementary to 18 bp preceding the transmembrane domain of the CD44-like protein receptor set out in FIGS. 1A–1B, including the stop codon. For the extracelluar domain the 3' primer has the sequence of 5' CGC GGT ACC TCA AGC CGT GGG GAC ACC TC 3' [SEQ ID NO:10], containing the underlined Asp718 restriction followed by nucleotides complementary to 18 bp preceding the stop codon of the CD44-like protein receptor set out in FIGS. 1A–1B, including the stop codon.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pA2 is used to express the CD44-like protein in the baculovirus expression system, using standard methods, such as those described in Summers et al., A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the Autographa californica nuclear polyhedrosis virus (AcMNPV) followed by convenient restriction sites. For an easy selection of recombinant virus the beta-galactosidase gene from E. coli is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzymes Sma I and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coil* HB101 cells are transformed with ligation mix and spread on culture plates. Bacteria are identified that contain the plasmid with the human CD44-like protein gene by digesting DNA from individual colonies using Bam HI and Asp718 and then analyzing the digestion product by gel electrophoresis. The sequence of the cloned fragment is confirmed by DNA sequencing. This plasmid is designated herein pBac/CD44-like protein.

5 μg of the plasmid pBac/CD44-like protein is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 μg of BaculoGold™ virus DNA and 5 μg of the plasmid pBac/CD44-like protein are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711)

seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted CD44-like protein receptor is identified by DNA analysis including restriction mapping and sequencing. This is designated herein as V-CD44-like protein.

Sf9 cells are grown in Grace's medium supplemented with 10% heat-inactivated FBS. The cells are infected with the recombinant baculovirus V-CD44-like protein at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of 35S-methionine and 5 µCi 35S cysteine (available from Amersham) are added. The cells are further incubated for 16 hours and then they are harvested by centrifugation, lysed and the labeled proteins are visualized by SDS-PAGE and autoradiography.

Example 4
Tissue Distribution of CD44-like Protein Expression

Northern blot analysis was carried out to examine the levels of expression of the gene encoding the CD44-like protein in human tissues, using methods described by, among others, Sambrook et al., cited above. A cDNA probe containing the entire nucleotide sequence of the CD44-like protein of the present invention (SEQ ID NO:1) was labeled with $^{32}$p using the rediprime™ DNA labelling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding the CD44-like protein.

Multiple Tissue Northern (MTN) blots containing various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots were mounted and exposed to film at –70° C. overnight, and films developed according to standard procedures.

Figure 3B:

As shown in FIGS. 3A and 3B, expression of the gene encoding the CD44-like protein of the present invention was detected in most human tissues. The levels of CD44-like mRNA were substantial in spleen, lymph node, fetal liver and placenta (FIG. 3A, lanes 1, 2 and 7, and FIG. 3B, lane 3, respectively), and lower levels of expression were also observed in appendix, bone marrow, lung, liver and skeletal muscle (FIG. 3A, lanes 4 and 6, and FIG. 3B, lanes 4, 5 and 6, respectively). The expression of CD44-like mRNA in thymus and peripheral blood leukocytes (FIG. 3A, lanes 3 and 5, respectively) was substantially less than that in other immune system tissues.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated nucleic acid molecule comprising a polynucleotide selected from the group consisting of:
   (a) a polynucleotide encoding amino acids from about −21 to about 301 of SEQ ID NO:2;
   (b) a polynucleotide encoding amino acids from about −20 to about 301 of SEQ ID NO:2;
   (c) a polynucleotide encoding amino acids from about 1 to about 301 of SEQ ID NO:2;
   (d) a polynucleotide encoding the same polypeptide encoded by the cDNA contained in ATCC Deposit No. 97520;
   (e) a polynucleotide encoding the same mature CD44-like polypeptide encoded by the cDNA contained in ATCC Deposit No. 97520;
   (f) a polynucleotide encoding amino acids from about 1 to about 217 of SEQ ID NO:2;
   (g) a polynucleotide encoding amino acids from about 246 to about 301 of SEQ ID NO:2;
   (h) a polynucleotide encoding amino acids from about 1 to about 217 and about 246 to about 301 of SEQ ID NO:2;
   (i) the polynucleotide complement of the polynucleotide of (a), (b), (c), (d), (e), (f), (g), or (h); and
   (j) a polynucleotide at least 95% identical to the polynucleotide of (a), (b), (c), (d), (e), (f), (g), (h), or (i).

2. The isolated nucleic acid molecule of claim 1, wherein said polynucleotide is (a).
3. The isolated nucleic acid molecule of claim 1, wherein said polynucleotide is (b).
4. The isolated nucleic acid molecule of claim 1, wherein said polynucleotide is (c).
5. The isolated nucleic acid molecule of claim 1, wherein said polynucleotide is (d).
6. The isolated nucleic acid molecule of claim 1, wherein said polynucleotide is (e).
7. The isolated nucleic acid molecule of claim 1, wherein said polynucleotide is (f).
8. The isolated nucleic acid molecule of claim 1, wherein said polynucleotide is (g).
9. The isolated nucleic acid molecule of claim 1, wherein said polynucleotide is (h).
10. The isolated nucleic acid molecule of claim 1, wherein said polynucleotide is (i).
11. The isolated nucleic acid molecule of claim 1, wherein said polynucleotide is (j).
12. The isolated nucleic acid molecule of claim 2, which comprises nucleotides 91 to 1056 of SEQ ID NO:1.
13. The isolated nucleic acid molecule of claim 3, which comprises nucleotides 94 to 1056 of SEQ ID NO:1.

14. The isolated nucleic acid molecule of claim 4, which comprises nucleotides 154 to 1056 of SEQ ID NO:1.

15. The isolated nucleic acid molecule of claim 7, which comprises nucleotides 154 to 804 of SEQ ID NO:1.

16. The isolated nucleic acid molecule of claim 8, which comprises nucleotides 889 to 1056 of SEQ ID NO:1.

17. The isolated nucleic acid molecule of claim 11, wherein said polynucleotide is at least 95% identical to the polynucleotide of (a).

18. The isolated nucleic acid molecule of claim 11, wherein said polynucleotide is at least 95% identical to the polynucleotide of (b).

19. The isolated nucleic acid molecule of claim 11, wherein said polynucleotide is at least 95% identical to the polynucleotide of (c).

20. The isolated nucleic acid molecule of claim 11, wherein said polynucleotide is at least 95% identical to the polynucleotide of (d).

21. The isolated nucleic acid molecule of claim 11, wherein said polynucleotide is at least 95% identical to the polynucleotide of (e).

22. The isolated nucleic acid molecule of claim 11, wherein said polynucleotide is at least 95% identical to the polynucleotide of (f).

23. The isolated nucleic acid molecule of claim 11, wherein said polynucleotide is at least 95% identical to the polynucleotide of (g).

24. The isolated nucleic acid molecule of claim 11, wherein said polynucleotide is at least 95% identical to the polynucleotide of (h).

25. The isolated nucleic acid molecule of claim 11, wherein said polynucleotide is at least 95% identical to the polynucleotide of (i).

26. An isolated nucleic acid molecule comprising 500 contiguous nucleotides from the coding region of SEQ ID NO:1.

27. The isolated nucleic acid molecule of claim 26, which comprises 550 contiguous nucleotides from the coding region of SEQ ID NO:1.

28. The isolated nucleic acid molecule of claim 27, which comprises 750 contiguous nucleotides from the coding region of SEQ ID NO:1.

29. An isolated nucleic acid molecule comprising a polynucleotide encoding a CD44-like polypeptide wherein, except for at least one conservative amino acid substitution, said polypeptide has an amino acid sequence selected from the group consisting of:
  (a) amino acids −21 to 301 of SEQ ID NO:2;
  (b) amino acids −20 to 301 of SEQ ID NO:2;
  (c) amino acids 1 to 301 of SEQ ID NO:2;
  (d) amino acids 1 to 217 of SEQ ID NO:2; and
  (e) amino acids 246 to 301 of SEQ ID NO:2.

30. The isolated nucleic acid molecule of claim 29, wherein said amino acid sequence is (a).

31. The isolated nucleic acid molecule of claim 29, wherein said amino acid sequence is (b).

32. The isolated nucleic acid molecule of claim 29, wherein said amino acid sequence is (c).

33. The isolated nucleic acid molecule of claim 29, wherein said amino acid sequence is (d).

34. The isolated nucleic acid molecule of claim 29, wherein said amino acid sequence is (e).

35. The isolated nucleic acid molecule of claim 1, which is DNA.

36. A method of making a recombinant vector comprising inserting a nucleic acid molecule of claim 1 into a vector in operable linkage to a promoter.

37. A recombinant vector produced by the method of claim 36.

38. A method of making a recombinant host cell comprising introducing the recombinant vector of claim 37 into a host cell.

39. A recombinant host cell produced by the method of claim 38.

40. A recombinant method of producing a CD44-like polypeptide, comprising culturing the recombinant host cell of claim 39 under conditions such that said polypeptide is expressed and recovering said polypeptide.

41. An isolated polypeptide comprising amino acids at least 95% identical to amino acids selected from the group consisting of:
  (a) amino acids from about −21 to about 301 of SEQ ID NO:2;
  (b) amino acids from about −20 to about 301 of SEQ ID NO:2;
  (c) amino acids from about 1 to about 301 of SEQ ID NO:2;
  (d) amino acids from about 1 to about 217 of SEQ ID NO:2;
  (e) amino acids from about 246 to about 301 of SEQ ID NO:2; and
  (f) amino acids from about 1 to about 217 and about 246 to about 301 of SEQ ID NO:2.

42. The isolated polypeptide of claim 41, which comprises amino acids at least 95% identical to amino acids −21 to 301 of SEQ ID NO:2.

43. The isolated polypeptide of claim 41, which comprises amino acids at least 95% identical to amino acids −20 to 301 of SEQ ID NO:2.

44. The isolated polypeptide of claim 41, which comprises amino acids at least 95% identical to amino acids 1 to 301 of SEQ ID NO:2.

45. The isolated polypeptide of claim 41, which comprises amino acids at least 95% identical to amino acids 1 to 217 of SEQ ID NO:2.

46. The isolated polypeptide of claim 41, which comprises amino acids at least 95% identical to amino acids 246 to 301 of SEQ ID NO:2.

47. The isolated polypeptide of claim 41, which comprises amino acids at least 95% identical to amino acids from about 1 to about 217 and about 246 to about 301 of SEQ ID NO:2.

48. The isolated polypeptide of claim 42, which binds hyaluronan.

49. The isolated polypeptide of claim 43, which binds hyaluronan.

50. The isolated polypeptide of claim 44, which binds hyaluronan.

51. The isolated polypeptide of claim 45, which binds hyaluronan.

52. The isolated polypeptide of claim 47, which binds hyaluronan.

53. An isolated CD-44 like polypeptide wherein, except for at least one conservative amino acid substitution, said polypeptide has an amino acid sequence selected from the group consisting of:
  (a) amino acids from about −21 to about 301 of SEQ ID NO:2;
  (b) amino acids from about −20 to about 301 of SEQ ID NO:2;
  (c) amino acids from about 1 to about 301 of SEQ ID NO:2;
  (d) amino acids from about 1 to about 217 of SEQ ID NO:2;

(e) amino acids from about 246 to about 301 of SEQ ID NO:2; and (f) amino acids from about 1 to about 217 and about 246 to about 301 of SEO ID NO:2.

54. The isolated polypeptide of claim 53, wherein said amino acid sequence is (a).

55. The isolated polypeptide of claim 53, wherein said amino acid sequence is (b).

56. The isolated polypeptide of claim 53, wherein said amino acid sequence is (c).

57. The isolated polypeptide of claim 53, wherein said amino acid sequence is (d).

58. The isolated polypeptide of claim 53, wherein said amino acid sequence is (e).

59. The isolated polypeptide of claim 53, wherein said amino acid sequence is (f).

60. The isolated polypeptide of claim 54, which binds hyaluronan.

61. The isolated polypeptide of claim 55, which binds hyaluronan.

62. The isolated polypeptide of claim 56, which binds hyaluronan.

63. The isolated polypeptide of claim 57, which binds hyaluronan.

64. The isolated polypeptide of claim 59, which binds hyaluronan.

65. An isolated polypeptide comprising amino acids selected from the group consisting of:

(a) amino acids −21 to 301 of SEQ ID NO:2;

(b) amino acids −20 to 301 of SEQ ID NO:2;

(c) amino acids 1 to 301 of SEQ ID NO:2;

(d) amino acids 1 to 217 of SEQ ID NO:2;

(e) amino acids 246 to 301 of SEQ ID NO:2; and (f) amino acids from about 1 to about 217 and about 246 to about 301 of SEO ID NO:2.

66. The isolated polypeptide of claim 65, which comprises amino acids −21 to 301 of SEQ ID NO:2.

67. The isolated polypeptide of claim 65, which comprises amino acids −20 to 301 of SEQ ID NO:2.

68. The isolated polypeptide of claim 65, which comprises amino acids 1 to 301 of SEQ ID NO:2.

69. The isolated polypeptide of claim 65, which comprises amino acids 1 to 217 of SEQ ID NO:2.

70. The isolated polypeptide of claim 65, which comprises amino acids 246 to 301 of SEQ ID NO:2.

71. The isolated polypeptide of claim 65, which comprises amino acids from about 1 to about 217 and about 246 to about 301 of SEQ ID NO:2.

72. The isolated polypeptide of claim 66, which is fused to Fc at the C-terminus.

73. The isolated polypeptide of claim 67, which is fused to Fc at the C-terminus.

74. The isolated polypeptide of claim 68, which is fused to Fc at the C-terminus.

75. The isolated polypeptide of claim 69, which is fused to Fc at the C-terminus.

76. The isolated polypeptide of claim 70, which is fused to Fc at the C-terminus.

77. The isolated polypeptide of claim 71, which is fused to Fc at the C-terminus.

78. An isolated polypeptide having an amino acid sequence identical to that encoded by the cDNA contained in ATCC Deposit No. 97520.

79. An epitope-bearing portion of the CD-44 like polypeptide of SEQ ID NO:2.

80. The epitope-bearing portion of claim 79, which comprises 30 contiguous amino acids of SEQ ID NO:2.

81. The epitope-bearing portion of claim 80, which comprises 50 contiguous amino acids of SEQ ID NO:2.

82. An isolated antibody that binds specifically to the polypeptide of claim 41.

83. An isolated antibody that binds specifically to a CD44-like polypeptide of claim 53.

84. An isolated antibody that binds specifically to the polypeptide of claim 65.

85. The isolated antibody of claim 82, which is monoclonal.

86. The isolated antibody of claim 83, which is monoclonal.

87. The isolated antibody of claim 84, which is monoclonal.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 2313 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 91..1056

(ix) FEATURE:
      (A) NAME/KEY: mat_peptide
      (B) LOCATION: 154..1056

(ix) FEATURE:
    (A) NAME/KEY: sig_peptide
    (B) LOCATION: 91..153

(xi) SEQUENCE DESCRIPTION: SEQ ID NO:1:

```
ACGAGCATCC GGACTAGTTA TTGAGCATCT GCCTCTCATA TCACCAGTGG CCATCTGAGG         60

TGTTTCCCTG CTCTGAAGG GGTAGGCACG ATG GCC AGG TGC TTC AGC CTG GTG         114
                                Met Ala Arg Cys Phe Ser Leu Val
                                -21 -20                      -15

TTG CTT CTC ACT TCC ATC TGG ACC ACG AGG CTC CTG GTC CAA GGC TCT         162
Leu Leu Leu Thr Ser Ile Trp Thr Thr Arg Leu Leu Val Gln Gly Ser
            -10              -5                            1

TTG CGT GCA GAA GAG CTT TCC ATC CAG GTG TCA TGC AGA ATT ATG GGG         210
Leu Arg Ala Glu Glu Leu Ser Ile Gln Val Ser Cys Arg Ile Met Gly
    5               10                  15

ATC ACC CTT GTG AGC AAA AAG GCG AAC CAG CAG CTG AAT TTC ACA GAA         258
Ile Thr Leu Val Ser Lys Lys Ala Asn Gln Gln Leu Asn Phe Thr Glu
20              25                  30                  35

GCT AAG GAG GCC TGT AGG CTG CTG GGA CTA AGT TTG GCC GGC AAG GAC         306
Ala Lys Glu Ala Cys Arg Leu Leu Gly Leu Ser Leu Ala Gly Lys Asp
                40                  45                  50

CAA GTT GAA ACA GCC TTG AAA GCT AGC TTT GCA ACT TGC AGC TAT GGC         354
Gln Val Glu Thr Ala Leu Lys Ala Ser Phe Ala Thr Cys Ser Tyr Gly
            55                  60                  65

TGG GTT GGC GAT GGA TTC GTG GTC ATC TCT AGG ATT AGC CCA AAC CCC         402
Trp Val Gly Asp Gly Phe Val Val Ile Ser Arg Ile Ser Pro Asn Pro
            70                  75                  80

AAG TGT GGG AAA AAT GGG GTG GGT GTC CTG ATT TGG AAG GTT CCA GTG         450
Lys Cys Gly Lys Asn Gly Val Gly Val Leu Ile Trp Lys Val Pro Val
    85                  90                  95

AGC CGA CAG TTT GCA GCC TAT TGT TAC AAC TCA TCT GAT ACT TGG ACT         498
Ser Arg Gln Phe Ala Ala Tyr Cys Tyr Asn Ser Ser Asp Thr Trp Thr
100             105                 110                 115

AAC TCG TGC ATT CCA GAA ATT ATC ACC ACC AAA GAT CCC ATA TTC AAC         546
Asn Ser Cys Ile Pro Glu Ile Ile Thr Thr Lys Asp Pro Ile Phe Asn
                120                 125                 130

ACT CAA ACT GCA ACA CAA ACA ACA GAA TTT ATT GTC AGT GAC AGT ACC         594
Thr Gln Thr Ala Thr Gln Thr Thr Glu Phe Ile Val Ser Asp Ser Thr
            135                 140                 145

TAC TCG GTG GCA TCC CCT TAC TCT ACA ATA CCT GCC CCT ACT ACT ACT         642
Tyr Ser Val Ala Ser Pro Tyr Ser Thr Ile Pro Ala Pro Thr Thr Thr
            150                 155                 160

CCT CCT GCT CCA GCT TCC ACT TCT ATT CCA CGG AGA AAA AAA TTG ATT         690
Pro Pro Ala Pro Ala Ser Thr Ser Ile Pro Arg Arg Lys Lys Leu Ile
165             170                 175

TGT GTC ACA GAA GTT TTT ATG GAA ACT AGC ACC ATG TCT ACA GAA ACT         738
Cys Val Thr Glu Val Phe Met Glu Thr Ser Thr Met Ser Thr Glu Thr
180             185                 190                 195

GAA CCA TTT GTT GAA AAT AAA GCA GCA TTC AAG AAT GAA GCT GCT GGG         786
Glu Pro Phe Val Glu Asn Lys Ala Ala Phe Lys Asn Glu Ala Ala Gly
                200                 205                 210

TTT GGA GGT GTC CCC ACG GCT CTG CTA GTG CTT GCT CTC CTC TTC TTT         834
Phe Gly Gly Val Pro Thr Ala Leu Leu Val Leu Ala Leu Leu Phe Phe
            215                 220                 225

GGT GCT GCA GCT GGT CTT GGA TTT TGC TAT GTC AAA AGG TAT GTG AAG         882
Gly Ala Ala Ala Gly Leu Gly Phe Cys Tyr Val Lys Arg Tyr Val Lys
            230                 235                 240

GCC TTC CCT TTT ACA AAC AAG AAT CAG CAG AAG GAA ATG ATC GAA ACC         930
Ala Phe Pro Phe Thr Asn Lys Asn Gln Gln Lys Glu Met Ile Glu Thr
245                 250                 255
```

| | | |
|---|---|---|
| AAA GTA GTA AAG GAG GAG AAG GCC AAT GAT AGC AAC CCT AAT GAG GAA | | 978 |
| Lys Val Val Lys Glu Glu Lys Ala Asn Asp Ser Asn Pro Asn Glu Glu | | |
| 260 265 270 275 | | |
| | | |
| TCA AAG AAA ACT GAT AAA AAC CCA GAA GAG TCC AAG AGT CCA AGC AAA | | 1026 |
| Ser Lys Lys Thr Asp Lys Asn Pro Glu Glu Ser Lys Ser Pro Ser Lys | | |
| 280 285 290 | | |
| | | |
| ACT ACC GTG CGA TGC CTG GAA GCT GAA GTT TAGATGAGAC AGAAATGAGG | | 1076 |
| Thr Thr Val Arg Cys Leu Glu Ala Glu Val | | |
| 295 300 | | |
| | | |
| AGACACACCT GAGGCTGGTT TCTTTCATGC TCCTTACCCT GCCCCAGCTG GGGAAATCAA | | 1136 |
| AAGGGCCAAA GAACCAAAGA AGAAAGTCCA CCCTTGGTTC CTAACTGGAA TCAGCTCAGG | | 1196 |
| ACTGCCATTG GACTATGGAG TGCACCAAAG AGAATGCCCT TCTCCTTATT GTAACCCTGT | | 1256 |
| CTGGATCCTA TCCTCCTACC TCCAAAGCTT CCCACGGCCT TTCTAGCCTG GCTATGTCCT | | 1316 |
| AATAATATCC CACTGGGAGA AAGGAGTTTT GCAAAGTGCA AGGACCTAAA ACATCTCATC | | 1376 |
| AGTATCCAGT GGTAAAAAGG CCTCCTGGCT GTCTGAGGCT AGGTGGGTTG AAAGCCAAGG | | 1436 |
| AGTCACTGAG ACCAAGGCTT TCTCTACTGA TTCCGCAGCT CAGACCCTTT CTTCAGCTCT | | 1496 |
| GAAAGAGAAA CACGTATCCC ACCTGACATG TCCTTCTGAG CCCGGTAAGA GCAAAAGAAT | | 1556 |
| GGCAGAAAAG TTTAGCCCCT GAAAGCCATG GAGATTCTCA TAACTTGAGA CCTAATCTCT | | 1616 |
| GTAAAGCTAA AATAAAGAAA TAGAACAAGG CTGAGGATAC GACAGTACAC TGTCAGCAGG | | 1676 |
| GACTGTAAAC ACAGACAGGG TCCAAGTGTT TTCTCTGAAC ACATTGAGTT GGAATCACTG | | 1736 |
| TTTAGAACAC ACACACTTAC TTTTTCTGGT CTCTACCACT GCTGATATTT TCTCTAGGAA | | 1796 |
| ATATACTTTT ACAAGTAACA AAAATAAAAA CTCTTATAAA TTTCTATTTT TATCTGAGTT | | 1856 |
| ACAGAAATGA TTACTAAGGA AGATTACTCA GTAATTTGTT TAAAAAGTAA TAAAATTCAA | | 1916 |
| CAAACATTTG CTGAATAGCT ACTATATGTC AAGTGCTGTG CAAGGTATTA CACTCTGTAA | | 1976 |
| TTGAATATTA TTCCTCAAAA AATTGCACAT AGTAGAACGC TATCTGGGAA GCTATTTTTT | | 2036 |
| TCAGTTTTGA TATTTCTAGC TTATCTACTT CCAAACTAAT TTTTATTTTT GCTGAGACTA | | 2096 |
| ATCTTATTCA TTTTCTCTAA TATGGCAACC ATTATAACCT TAATTTATTA TTAACATACC | | 2156 |
| TAAGAAGTAC ATTGTTACCT CTATATACCA AAGCACATTT TAAAAGTGCC ATTAACAAAT | | 2216 |
| GTATCACTAG CCCTCCTTTT TCCAACAAGA AGGGACTGAG AGATGCAGAA ATATTTGTGA | | 2276 |
| CAAAAAATTA AAGCATTTAG AAAAAAAAAA AAAAAAA | | 2313 |

(2) INFORMATION FOR SEQ ID NO:2:

(i) SEQUENCE CHARACTERISTICS:
        (A) LENGTH: 322 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Arg Cys Phe Ser Leu Val Leu Leu Thr Ser Ile Trp Thr
-21 -20        -15            -10

Thr Arg Leu Leu Val Gln Gly Ser Leu Arg Ala Glu Glu Leu Ser Ile
-5              1              5              10

Gln Val Ser Cys Arg Ile Met Gly Ile Thr Leu Val Ser Lys Lys Ala
            15              20              25

Asn Gln Gln Leu Asn Phe Thr Glu Ala Lys Glu Ala Cys Arg Leu Leu
        30              35              40

Gly Leu Ser Leu Ala Gly Lys Asp Gln Val Glu Thr Ala Leu Lys Ala
        45              50              55

```
Ser Phe Ala Thr Cys Ser Tyr Gly Trp Val Gly Asp Gly Phe Val Val
 60              65                  70                  75

Ile Ser Arg Ile Ser Pro Asn Pro Lys Cys Gly Lys Asn Gly Val Gly
                 80                  85                  90

Val Leu Ile Trp Lys Val Pro Val Ser Arg Gln Phe Ala Ala Tyr Cys
                 95                 100                 105

Tyr Asn Ser Ser Asp Thr Trp Asn Ser Cys Ile Pro Glu Ile Ile
                110                 115                 120

Thr Thr Lys Asp Pro Ile Phe Asn Thr Gln Thr Ala Thr Gln Thr Thr
            125                 130                 135

Glu Phe Ile Val Ser Asp Ser Thr Tyr Ser Val Ala Ser Pro Tyr Ser
140                 145                 150                 155

Thr Ile Pro Ala Pro Thr Thr Thr Pro Pro Ala Pro Ala Ser Thr Ser
                160                 165                 170

Ile Pro Arg Arg Lys Lys Leu Ile Cys Val Thr Glu Val Phe Met Glu
            175                 180                 185

Thr Ser Thr Met Ser Thr Glu Thr Glu Pro Phe Val Glu Asn Lys Ala
            190                 195                 200

Ala Phe Lys Asn Glu Ala Ala Gly Phe Gly Gly Val Pro Thr Ala Leu
            205                 210                 215

Leu Val Leu Ala Leu Leu Phe Phe Gly Ala Ala Gly Leu Gly Phe
220                 225                 230                 235

Cys Tyr Val Lys Arg Tyr Val Lys Ala Phe Pro Phe Thr Asn Lys Asn
                240                 245                 250

Gln Gln Lys Glu Met Ile Glu Thr Lys Val Val Lys Glu Glu Lys Ala
            255                 260                 265

Asn Asp Ser Asn Pro Asn Glu Glu Ser Lys Lys Thr Asp Lys Asn Pro
            270                 275                 280

Glu Glu Ser Lys Ser Pro Ser Lys Thr Thr Val Arg Cys Leu Glu Ala
            285                 290                 295

Glu Val
300

(2) INFORMATION FOR SEQ ID NO:3:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Asp Lys Val Trp Trp His Thr Ala Trp Gly Leu Leu Cys Leu Leu
1               5                  10                  15

Gln Leu Ser Leu Ala Gln Gln Gln Ile Asp Leu Asn Ile Thr Cys Arg
                20                  25                  30

Tyr Ala Gly Val Phe His Val Glu Lys Asn Gly Arg Tyr Ser Ile Ser
            35                  40                  45

Arg Thr Glu Ala Ala Asp Leu Cys Glu Ala Phe Asn Thr Thr Leu Pro
50                  55                  60

Thr Met Ala Gln Met Glu Leu Ala Leu Arg Lys Gly Phe Glu Thr Cys
65                  70                  75                  80

Arg Tyr Gly Phe Ile Glu Gly His Val Val Ile Pro Arg Ile His Pro
                85                  90                  95
```

```
Asn Ala Ile Cys Ala Ala Asn Asn Thr Gly Val Tyr Ile Leu Leu Ala
                100                 105                 110
Ser Asn Thr Ser His Tyr Asp Thr Tyr Cys Phe Asn Ala Ser Ala Pro
            115                 120                 125
Leu Glu Glu Asp Cys Thr Ser Val Thr Asp Leu Pro Asn Ser Phe Asp
130                 135                 140
Gly Pro Val Thr Ile Thr Ile Val Asn Arg Asp Gly Thr Arg Tyr Ser
145                 150                 155                 160
Lys Lys Gly Glu Tyr Arg Thr His Gln Glu Asp Ile Asp Ala Ser Asn
                165                 170                 175
Ile Ile Asp Glu Asp Val Ser Ser Gly Ser Thr Ile Glu Lys Ser Thr
                180                 185                 190
Pro Glu Gly Tyr Ile Leu His Thr Asp Leu Pro Thr Ser Gln Pro Thr
                195                 200                 205
Gly Asp Arg Asp Asp Ala Phe Phe Ile Gly Ser Thr Leu Ala Thr Gly
210                 215                 220
His Ser Ser Gly Asn Gln Asp Ser Gly Val Thr Thr Ser Gly Pro
225                 230                 235                 240
Ala Arg Arg Pro Gln Ile Pro Glu Trp Leu Ile Ile Leu Ala Ser Leu
                245                 250                 255
Leu Ala Leu Ala Leu Ile Leu Ala Val Cys Ile Ala Val Asn Ser Arg
            260                 265                 270
Arg Arg Cys Gly Gln Lys Lys Lys Leu Val Ile Asn Ser Gly Asn Gly
            275                 280                 285
Thr Val Glu Asp Arg Lys Pro Ser Glu Leu Asn Gly Glu Ala Ser Lys
            290                 295                 300
Ser Gln Glu Met Val His Leu Val Asn Lys Glu Pro Thr Glu Thr Pro
305                 310                 315                 320
Asp Gln Phe Met Thr Ala Asp Glu Thr Arg Asn Leu Gln Ser Val Asp
                325                 330                 335
Met Lys Ile (2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CGCCCATGGT CCAAGGCTCT TTGCGT                                              26

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGCAAGCTTT CAAGCCGTGG GGACACCTC                                           29

(2) INFORMATION FOR SEQ ID NO:6:
```

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCGGATCCG CCATCATGGC CAGGTGCTTC AGC                                     33

(2) INFORMATION FOR SEQ ID NO:7:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CGCTCTAGAT CAAGCGTAGT CTGGGACGTC GTATGGGTAA GCCTGGGGGA CACCTC           56

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGCGGTACCT CAACCAGCCT CAGGTGT                                           27

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGCGGATCCG CCATCATGGC CAGGTGCTTC AGC                                     33

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCGGTACCT CAAGCCGTGG GGACACCTC                                         29

(2) INFORMATION FOR SEQ ID NO:11:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | | | | | |
|---|---|---|---|---|---|
| AGTGATTCCA | ACTCAATGTG | TTCAGAGAAA | ACACTTTGAC | CCTGTCTGTG | TTTACAGTCC | 60 |
| CTGCTGACAG | TGTACTGTCG | TATCCTCAGC | CTTGTTCTAT | TTCTTTATTT | NAGCTTTACA | 120 |
| GAGATTAGGT | CTCAAGTTAT | GAGANTCTCC | ATGGCTTTCA | GGGGCTAAAC | TTTTCTGCCA | 180 |
| TTCTTTTGCT | CTTACCGGGC | TCAGAAGGAC | ATGTCAGGTG | GGATACGTGT | TTCTCTTTCA | 240 |
| GAGCTGAAGN | AAGGGTCTGA | GCTGCGGAAT | CAGTAGAGNA | AGCCTTGGTC | TCAGTGACTC | 300 |
| CTTNGCTTTC | AACCCACCTA | GCCTCAGACA | GCCAGGAGG | | | 339 |

(2) INFORMATION FOR SEQ ID NO:12:

(i) SEQUENCE CHARACTERISTICS:
            (A) LENGTH: 492 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

| | | | | | |
|---|---|---|---|---|---|
| AATTCGGCAC | GAGCATCCGG | ACTAGTTATT | GAGCATCTGC | CTCTCATATC | ACCAGTGGCC | 60 |
| ATCTGAGGTG | TTTCCCTGGC | TCTGAAGGGG | TNGGCACGAT | GGCCAGGTGC | TTCAGCCTGG | 120 |
| TGTTGCTTNT | CACTTCCATC | TGGACCACGA | GGCTCCTGGT | CCAAGGCTCT | TTGCGTGCAG | 180 |
| AAGAGCTTTC | CATCCAGGTG | TCATGCAGAA | TTATGGGGAT | CACCCTTGTG | AGCAAAAAGG | 240 |
| CGAACCAGCA | GCTGAATTTC | ACAGAAGCTA | AGGAGGCCTG | TAGGTTGCTN | GGACTAAGTT | 300 |
| TGGCCGGCAA | GGCCCAGTTG | AACAGCTTGA | AAGTAGCTTT | GAAATTGCAG | TTTGGCTTGG | 360 |
| TTGGGATGGT | TCGNGNCATT | TAGGTTAGCC | CAACCCANTT | TGGAAANTGG | GTGGNNCNAT | 420 |
| TTGNAGTCCC | TTAGCCCNAT | TTCAGCTTTT | TNAACATTGA | TTGGNAATGG | ATCCAATTTC | 480 |
| CCAGCCTTAA | NA | | | | | 492 |

(2) INFORMATION FOR SEQ ID NO:13:

(i) SEQUENCE CHARACTERISTICS:
            (A) LENGTH: 466 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

| | | | | | |
|---|---|---|---|---|---|
| AATTCGGCAG | AGGATTTGTT | GAAAATAAAG | CAGCATTCAA | GAATGAAGCT | GCTGGGTTTG | 60 |
| GAGGTGTCCC | CACGGCTCTG | CTAGTGCTTG | CTCTCCTCTT | CTTTGGTGCT | GCAGCTGGTC | 120 |
| TTGGATTTTG | CTATGTCAAA | AGGTATGTGA | AAGGCCTTCC | CTTTTACAAA | CAAGAATCNG | 180 |
| CAGAAGGGAA | ATGATCGAAA | CCAAAGTAGT | GAAAGGAGGA | GAAGGCCAAT | GNTAGCAACC | 240 |
| CTGAATGAGG | GATTCAAAGG | AAAACTGNTT | AAAAACCCAG | TAGNAGTTCC | AAGAGTNCCA | 300 |
| AGCAAAACTT | ACCGTGTCGA | TGCCTGGGNA | GCTGNNAGTT | TTAGGTGGAG | ACAGTAANNG | 360 |
| ANGGNNGNCA | CACCTNAGGG | TTGGTTTTCT | TTTCAGGTTC | CNTTTACCCT | NGGNCCCAAN | 420 |
| NTNGGGGGTA | AATTCAAAAA | GGGGGNCCAA | GGANCCCAAG | GTTTTG | | 466 |

(2) INFORMATION FOR SEQ ID NO:14:

(i) SEQUENCE CHARACTERISTICS:
         (A) LENGTH: 239 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:14:

| | | | | | |
|---|---|---|---|---|---|
| CTAAATGCTT | TAATTTTTTG | TCACAAATAT | TTCTGCATCT | CTCAGTCCCT | TCTTGTTGGA | 60 |
| AAAAGGAGGG | CTAGTGATAC | ATTTGTTAAT | GGCACTTTTA | AAANGTGCTT | TGGTATATAG | 120 |
| AGGNAACAAT | GTACTTCNNA | GGNATGTTAA | TAATAAATTA | AGGTTATAAT | GGTTGCCATA | 180 |
| TCNGAGNGAA | TGNATAAGAT | TAGTCTCAGC | AAAAACAAAA | ATTAGTTTGG | AAGTAGATA | 239 |

(2) INFORMATION FOR SEQ ID NO:15:

(i) SEQUENCE CHARACTERISTICS:
         (A) LENGTH: 498 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:15:

| | | | | | |
|---|---|---|---|---|---|
| AATTCGGCAG | AGNCTTGGAT | TTTGCTATGT | CAAAAGGTAT | GTNAAGGCCT | TCCCTTTTAC | 60 |
| AAACAAGAAT | CAGCAGAAGG | AAATGATCGA | AACCAAAGTA | GTAAAGGAGG | AGAAGGCCAA | 120 |
| TGAATAGCAA | CCCTAATGAG | GAATCAAAGA | AAACTGATAA | AAACCCAGTA | AGAGTCCAAG | 180 |
| AGTCCAAGCA | AAACTTACCG | TGNCGNATGC | CTGGAAGCTG | GAAGTTTTAG | ATGGAGGACA | 240 |
| GAAATGAGGG | GGACACACCT | GAGGGCTGGT | TTCTTTNCAT | GCTTCCTTNA | CCCTGNCCCC | 300 |
| AGCTGGGGGG | ANAATCCAAA | AGGGGCCCAN | AGNAACCCAA | AGGNGGGAAN | GTTCCNNCCC | 360 |
| TTTNGGTTTC | CCTNAACTNG | GGGATTCCNG | TTTCCAGGGA | NTTTCNCTTT | NGGGNNTTTT | 420 |
| GGGGGTNGNC | ANCCCAAGGG | GGATNGNCCC | TTTTTCCCTT | ATTTGTTAAN | CCCTGTTTTT | 480 |
| GGGTCCCTNT | NCTGNTTA | | | | | 498 |